United States Patent
Imran

(10) Patent No.: US 11,103,187 B2
(45) Date of Patent: Aug. 31, 2021

(54) SWALLOWABLE CAPSULE, SYSTEM AND METHOD FOR MEASURING GASTRIC EMPTYING PARAMETERS

(71) Applicant: Rani Therapeutics, LLC, San Jose, CA (US)

(72) Inventor: Mir A. Imran, Los Altos Hills, CA (US)

(73) Assignee: Rani Therapeutics, LLC, San Jose, CA (US)

(*) Notice: Subject to any disclaimer, the term of this patent is extended or adjusted under 35 U.S.C. 154(b) by 512 days.

(21) Appl. No.: 16/006,093

(22) Filed: Jun. 12, 2018

(65) Prior Publication Data

US 2018/0353133 A1 Dec. 13, 2018

Related U.S. Application Data

(60) Provisional application No. 62/518,246, filed on Jun. 12, 2017.

(51) Int. Cl.
*A61B 5/00* (2006.01)
*A61B 5/07* (2006.01)
(Continued)

(52) U.S. Cl.
CPC ............ *A61B 5/6861* (2013.01); *A61B 5/036* (2013.01); *A61B 5/073* (2013.01);
(Continued)

(58) Field of Classification Search
CPC ..... A61B 5/6861; A61B 5/036; A61B 5/4238; A61B 5/073; A61B 5/4255; A61B 5/14539; A61B 2562/0247
(Continued)

(56) References Cited

U.S. PATENT DOCUMENTS 3,739,279 A  6/1973 Hollis et al.
5,187,154 A  2/1993 Phillips et al.
(Continued)

FOREIGN PATENT DOCUMENTS

CN  102307536 A  1/2012
EP  2087831 A1  8/2009
(Continued)

OTHER PUBLICATIONS

Koch et al. (Diabetic Gastroparesis, Gastroenterol Clin North Am. Mar. 2015;44(1):39-57) (Year: 2015).*
(Continued)

*Primary Examiner* — Jacqueline Cheng
*Assistant Examiner* — Tho Q Tran
(74) *Attorney, Agent, or Firm* — Wilson Sonsini Goodrich & Rosati

(57) ABSTRACT

Embodiments provide devices, systems and methods for measuring a gastric emptying (GE) parameter (GEP). Many embodiments provide a swallowable capsule having three electrodes one covered by a coating which remains in the stomach but is degraded in the small intestine (SI). The electrodes are coupled to circuitry such that when the capsule is in the stomach, current flow occurs between the first two electrodes generating a first signal and in the SI current flow occurs between the second and now uncovered third electrode generating a second signal. These two signals can be transmitted and analyzed externally or by an internal controller to determine a GEP e.g., GE time. The patient may wear an external device configured to receive and analyze the signals to determine GE time. Embodiments of the invention may be used to diagnose gastroparesis and provide patient's information on when to eat meals or administer insulin after eating.

45 Claims, 11 Drawing Sheets

(51) Int. Cl.
*A61B 5/145* (2006.01)
*A61B 5/03* (2006.01)
(52) U.S. Cl.
CPC ........ *A61B 5/14539* (2013.01); *A61B 5/4238* (2013.01); *A61B 5/4255* (2013.01); *A61B 2562/0247* (2013.01)
(58) Field of Classification Search
USPC ........................................................ 600/361
See application file for complete search history.

(56) References Cited

U.S. PATENT DOCUMENTS

| | | |
|---|---|---|
| 7,160,258 B2 | 1/2007 | Imran et al. |
| 8,005,536 B2 | 8/2011 | Imran et al. |
| 8,055,334 B2 | 11/2011 | Savage et al. |
| 8,303,490 B2 | 11/2012 | Kawano et al. |
| 8,360,976 B2 | 1/2013 | Imran et al. |
| 8,617,070 B2 | 12/2013 | Imran et al. |
| 8,816,814 B2 | 8/2014 | Hyde et al. |
| 8,945,010 B2 | 2/2015 | Semler et al. |
| 9,095,261 B2 | 8/2015 | Kawano et al. |
| 9,167,990 B2 | 10/2015 | Imran et al. |
| 9,168,000 B2 | 10/2015 | Dunki-Jacobs et al. |
| 9,456,774 B2 | 10/2016 | Imran et al. |
| 2006/0243288 A1 | 11/2006 | Kim et al. |
| 2011/0040203 A1 | 2/2011 | Savage et al. |
| 2011/0306544 A1* | 12/2011 | Sukhotnik ................. A61P 3/00 514/5.9 |
| 2014/0343378 A1 | 11/2014 | Arneson et al. |
| 2019/0351202 A1* | 11/2019 | Melamud ............ A61M 31/002 |

FOREIGN PATENT DOCUMENTS

| | | |
|---|---|---|
| EP | 2489300 B1 | 7/2015 |
| WO | WO-2010090986 A2 | 8/2010 |
| WO | WO-2018131036 A1 | 7/2018 |

OTHER PUBLICATIONS

Ferrua, et al. Modeling the fluid dynamics in a human stomach to gain insight of food digestion. J Food Sci. Sep. 2010;75(7):R151-62. doi: 10.1111/j.1750-3841.2010.01748.x.

Iltz, et al. Exenatide: an incretin mimetic for the treatment of type 2 diabetes mellitus. Clin Ther. May 2006;28(5):652-65.

International search report with written opinion dated Aug. 28, 2018 for PCT/US18/37153.

European search report and opinion dated Mar. 11, 2021 for EP Application No. 18818502.9.

* cited by examiner

SWALLOWABLE CAPSULE, SYSTEM AND METHOD FOR MEASURING GASTRIC EMPTYING PARAMETERS

CROSS-REFERENCE TO RELATED APPLICATIONS

This application claims the benefit of priority of U.S. Provisional Patent Application Ser. No. 62/518,246, entitled "Swallowable Capsule, System and Method For Measuring Gastric Emptying Parameters", filed Jun. 12, 2017, which is fully incorporated herein by references for all purposes.

BACKGROUND OF THE INVENTION

Field of the Invention

Embodiments described herein relate to devices, systems and methods for measuring physiologic parameters of the gastro-intestinal system. More specifically embodiments of the invention relate to devices, systems and methods for measuring gastric emptying parameters such as gastric emptying time.

There are a number of conditions which can affect the proper digestion and function of the gastro-intestinal tract of a human or other mammal. One of them, gastroparesis, also known as delayed gastric emptying, is a condition characterized by multiple symptoms, including nausea, vomiting, bloating, abdominal pain or discomfort and early satiety. Diagnosing gastroparesis is traditionally determined from a combination of symptom assessment and gastric emptying scintigraphy. In particular, this method can be used to measure gastric emptying time, or the time it takes for food to be emptied from the stomach into the small intestine after being eaten. Gastro duodenal manometry may also be performed to provide further evidence of the condition. Gastro duodenal manometry is an invasive, catheter-based system in which a manometry probe is inserted through a patient's nose or mouth into the GI tract. The manometry probe usually has a suite of pressure sensors located at fixed positions along its length. These pressure sensors detect and send contraction amplitude and frequency data through connected Wires to an external recording device. For placement of the probe, this technique is uncomfortable for the patient and requires the patient to be sedated and physically connected to the detector. Besides being highly uncomfortable, the manometry measurement system directly impacts the normal functioning of the patient which may skew the manometry results.

Thus for the reasons above, there is a need for improved systems and method for measurement of gastric emptying time as well as a means for diagnosing gastroparesis.

SUMMARY OF THE INVENTION

Embodiments of the invention provide devices, systems and methods for measuring a gastric emptying parameter (GEP) such as gastric emptying time. Many embodiments provide a swallowable capsule having three electrodes one covered by a coating which remains in the stomach but is degraded in the small intestine (SI). The electrodes are coupled to circuitry such that when the capsule is in the stomach, current flow occurs between the first two electrodes generating a first signal and in the SI current flow occurs between the second and now uncovered third electrode generating a second signal. These two signals can be transmitted and analyzed by an external device or an internal controller to determine a gastric emptying time or other gastric emptying parameter. The patient may wear an external device configured to receive and analyze the two signals and provide the patient and/or medical provider with information on gastric emptying time or other gastric emptying parameter.

Embodiments of the invention are particularly useful in diagnosing patients with gastroparesis or related conditions and providing those patients with information on eating patterns, e.g., portion sizes and times between portions, so as to minimize the adverse symptoms of the condition (e.g., nausea). They may also be used to provide patients who have glucose regulation disorders such diabetes with information on when to administer their insulin (or other glucose regulating compound) after they eat a meal.

In a first aspect, embodiments of the invention provide swallowable devices such as swallowable capsules for the measurement of gastric emptying time or other gastric emptying parameter. An embodiment of such a capsule comprises a capsule body sized to be swallowed and pass through the intestinal track of a patient. The capsule body defines a capsule interior for positioning of one or more components of the capsule. The capsule body desirably comprise various biocompatible polymers known in the art which are not broken down in the GI tract, suitable examples including polycarbonate. The capsule body may also have imaging markers such as radio-opaque or echogenic markers so as to be visible under fluoroscopy or ultrasound. Also the entire capsule body may be from radio-opaque or echogenic materials or otherwise comprise such materials. Two or more electrodes may be positioned on the capsule body in various arrangements so as to couple to and have current flow through the fluids present in the organs of the GI tract such as those in the stomach or small intestine. The electrodes may comprise one or more biocompatible conductive metals known in the medical device arts such as stainless steel or gold alloys and they may be attached to capsule body using various biocompatible adhesives. In specific embodiments, at least a first, second and third electrodes disposed are disposed on an outer surface of the capsule body. In preferred embodiments, the electrodes are linearly aligned with respect to a longitudinal axis of the capsule, though radial alignments and non-aligned configurations are also considered. Also preferably, they are spaced equidistantly (e.g., in range from about 1 mm to 10 mm), so that the distance between first and second electrodes is about the same as between the second and third electrode. However, in some embodiment non-equidistant configurations may be used. For example, in some embodiments, the second and third electrodes can be spaced closer to provide for reduced resistance for the flow of electrical current between the second and third electrodes when the device is in the small intestine which may contain less conductive fluids/medium for completing a circuit between electrodes vs the stomach which contains more conductive fluids by virtue of its acid and higher fluid content.

An enteric electrically insulative coating is disposed over a portion of the capsule body outer surface including the third electrode. The coating is configured to protect and electrically insulate the third electrode while in the stomach and degrade in response to a selected pH in the small intestine to expose the third electrode to the fluids in the small intestine. The capsule body interior contains a first circuit electrically coupled to the first and second electrodes and a second circuit coupled to the second and third electrodes. A controller, also disposed in the capsule body, is electrically coupled to both circuits. The circuits typically include an operational amplifier (opamp) and at least three resistors, which may be arranged in a voltage divider configuration. The opamp receives an input signal from a node of the respective circuit including the first or third electrodes, amplifies it and sends the output signal as an input signal to the controller. The resistors may have values above 1 to 10 mega Ohm. The circuits may also include a capacitor to ensure that current which flows between the electrodes in the stomach or small intestine is an AC current. The circuits also receive a driver input voltage from the controller.

The circuits can be configured to perform one or more functions used in measuring GET or other GE parameter. In particular, the first circuit is configured to generate a first input signal when there is current flow between the first and second electrodes and the second circuit is configured to generate a second input signal based when there is current flow between the second and third electrodes. As is explained below, current flow occurs in the first circuit when the first and second electrodes come into contact with conductive fluids in the stomach such as stomach acids. When this happens, the first circuit starts to generate an input signal to the controller which provides an indication of when the capsule has reached the stomach after being swallowed. Similarly, current flows in the second circuit after the insulative coating degrades in the small intestine and the second and third electrodes come into contact with conductive fluids in the small intestine. When this happens, the second circuit generates an input signal to the controller which provides an indication of when the capsule has reached the small intestine. Information from these two signals, including their start times, can then be used to determine gastric emptying time or another gastric emptying parameter. In particular embodiments the start times can be determined using a clock device integral or otherwise coupled to the controller. In particular, the start time of the first input signal can be subtracted from the start time of the second signal to arrive at gastric emptying time. In particular embodiments, allowances can be made for the estimated time it takes for the enteric coating to degrade in the small intestine, as well other factors. Such allowances can be incorporated into a module for determination of gastric emptying time which may be resident on a controller of an external device or the controller in the capsule.

The controller, which may correspond to a microprocessor or analogue device, is coupled to both circuits as well as power source such as a lithium ion or other chemical storage battery. The controller may also include or be coupled to a transmitter such as an RF transmitter, for transmitting signals encoding information from the controller, (e.g., GET) to a receiver on an external device. In some embodiments the controller may include a low power RF generator and the transmitter may correspond to a power amplifier which amplifies the low power RF signal coming from the controller.

The controller may be configured to perform a number functions either via hardware or software. In particular it may be configured to generate and/or utilize a clock signal for determining the start times of the first and second signals. The clock signal may be single phase or multiphase. Also in some embodiments, the clock signal can be generated by an analog-to-digital converters. The controller will also typically be configured to generate a driver signal sent to the second electrode and receive the signals from the first and second circuits when current is flowing through them. Typically, the driver signal is in the form of an AC voltage with very low amperage in the milliamp range, more preferably in the micro-amp and voltage in the range from 0.5 to 2 volts with other ranges contemplated. The controller is further configured to generate a first output signal in response to the first input signal from the first circuit and a second output signal in response to the second output signal from the second circuit. The respective output signals will typically be in AC form and configured for transmission by the RF or other transmitter integral to or otherwise coupled to the controller. These signals may be generated by the controller itself or a signal generator electrically coupled to the controller. In particular embodiments, the output signals may correspond to distinctive chirp signals known in the signal processing arts. In one particular embodiment, the first output signal may correspond to an up chirp signal and the second signal a down chirp signal. The controller can also control how long a respective output signal is generated once it starts. For example, it can stop the first output signal after a selected period of time after that signal starts. It may also do the same for the second output signal. The time periods, which may be in the range of 1 to 20 second, more particularly 1 to 10 seconds are selected to provide sufficient time for detection and recording by an outside receiver or the controller itself, as well as conserve battery power.

The controller may also include logic in hardware or software for recording and storing the start time and other information on the first and second input signals such as their amplitudes. The controller may also include logic in hardware or software for calculating gastric emptying times (GET) or other GE parameter using approaches described herein. For software implementations, the logic may be in the form of a software module resident in the controller (e.g., in RAM, ROM or other memory) which includes algorithms calculation of GET. The same module, herein a GET module, may also be resident on controller on an external device worn by the patient. In addition to calculation of GET by the subtraction method described above, the module may include algorithms for calculation of GET which take into account other factors such as how long it takes for the enteric coating to dissolve, and the amount, type and time of any food eaten before, during or after the capsule was ingested. This information can be used to make allowances for longer or shorter gastric empting times for the type and amount of food eaten. For example, liquid vs solid meals and protein rich foods which leave the stomach sooner than foods high in carbohydrates, while food high in lipids (e.g., fat) take the longest to leave the stomach. In some embodiments, including those where GET calculation is done by a controller on an external device, the patient may enter this information (e.g. using an external device such as a tablet, cell phone, etc.) including the nutritional information and portion size. The controller, including the module, may also include programming or other logic for calculation of other GE parameters including one or more of, GE velocity, the speed at which food/stomach contents moves from the stomach to the small intestine; average GE velocity, peak GE velocity, GET peristaltic contraction ratio; which is the ratio of GE time per number of peristaltic contractions; and GET average peristaltic force ratio, which is ratio of GET time per average force of peristaltic contraction occurring prior to or during the transit of food from the stomach to the small intestine.

However in other embodiments, including those where the GET module is resident in the controller on the capsule, a specific procedure can be followed by the patient where the patient is given a test kit (herein a GET test kit) containing a capsule and a matched prepackaged GET test meal having known parameters including for example a known portion size and known amounts of carbohydrates, protein, fat etc.

These or other nutritional parameters comprise test meal information. The test meal information including portion size and nutritional information (e.g., protein content etc.) are pre-entered into the GET module. The patient is also instructed to eat the meal with the capsule or at a set time interval before or after ingestion of the capsule. The test meal information may then be used by the GET module to adjust the measurement of GET accordingly (e.g., increase it or decrease it). For example, for higher for larger and/or denser meals the GET module may decrease the ultimately determined GET to reflect that the fact that denser foods and/or larger portion sizes may take more time to move through the stomach. The converse being the case for smaller and/or less dense meals. In some embodiments, the capsule may actually be embedded or otherwise surrounded by the test meal, ensuring that both are taken concurrently for embodiments where that is the desired approach. Embodiments using such a GET test kit provide the benefit of reduced variability in gastric emptying due to the patient's eating habits and thus a more accurate result for GET or other GE parameter.

In another aspect, the invention provides a system for measurement of GET or other GE parameter comprising embodiments of the swallowable capsule described herein and an external receiver unit which may be configured to be worn or carried by the patient. The receiver unit will typically include a receiver such as an RF receiver for receiving the transmitted output and other signals by the capsule. The receiver unit may also comprise and ultrasound receiver as well. It will also include a controller (e.g., a microprocessor) which may include hardware and/or software such as a GET module for analyzing the transmitted signals from the capsule and determining GE times using one more approaches described herein. The external receiver unit may also include audio alarms or displays for alerting the patient when capsule has reached the stomach (by detecting the first output signal) and when it has reached the small intestine (by detecting the second output signal). The controller may also be programmed to display the calculated GE time or other GE parameter for use by the patient or medical provider.

In addition to the above features, the receiving unit may have communication ability itself for example, WIFI ability using a BLUETOOTH protocol so as to allow for communication and data sharing with other WIFI enabled devices such as cell phones, smart phones, tablets and the like. In one implementation, the receiver unit can be configured to communicate and share data with a smart phone so that the patient can upload their GET and related data to their smart phone and then send that data over the INTERNET or other network to their physician or other medical care provider.

In some embodiments, the receiver unit may comprise or be incorporated into an adhesive patch worn by the patient, for example, over the abdominal area to facilitate communication between the receiver and the capsule. The patch may contain just the receiver or other components as well such as the controller. The patch may also be configured to wirelessly communicate with another external computational device such as a tablet device or smart phone (e.g. by a BLUETOOTH protocol described below) which receives information (e.g., information contained in the first or second signals) from the patch and performs various computations to determine GE time or other GE parameter. Use of the patch provides the benefit of improved signal receipt by the receiver (due to proximity) while still allowing the patient to see GE times and enter information, e.g., meal content and times.

In various embodiments, the enteric coating is selected to degrade in the pH of the small intestine to expose the third electrode so that the third electrode along with the second electrode electrically couple with the contents in the small intestine to allow current to flow between the two electrodes. Also the coating can be configured to degrade within a selected portion of the small intestine based on pH. For example, in particular embodiments, the coating can be configured to degrade above a pH of about 5.5 for the duodenum or above a pH of 6.5 to 6.8 in the jejunum. In preferred embodiments, the coating is configured to degrade above a pH of about 6.5. In various embodiments, the pH sensitive coatings may correspond to EUDRAGIT coatings and others known in the art which degrade in response to specific pH's in specific location in the GI tract, such as more acid pH in the stomach (1.5-3.5) and increasingly less acidic pH in the small intestine (5.5 in the duodenum and 6.5-6.8 in the jejunum). In particular embodiments the EUDRAGIT coating is selected to degrade above a pH of about 6.5.

In yet another aspect, the invention provides a GET test kit including an embodiment of the swallowable capsule described herein and a test meal. The portion size and constituent components of the test meal (e.g., amount of fat, protein etc.) are preselected and matched to the particular swallowable capsule, for example, in terms of size of capsule and the positioning of the electrodes on the capsule. The nutritional information and portion size of the test meal (described herein as test meal information) can also be stored in memory of the capsule microprocessor or other controller so that that information can be used in an algorithm for calculation of GE time or other GE parameter. In some embodiments, the capsule and test meal are separate, while in others the capsule is incorporated into the test meal either by being surrounded by the food material of the test meal or embedded or attached to a surface of the test meal.

In yet another aspect, the invention provides various methods for measuring GE time or other GE parameter using embodiments of the swallowable capsule described herein. In an exemplary embodiment of such a method a patient for whom a GE parameter is to be measured ingests an embodiment of the swallowable capsule described configured to transmit a first electrical signal when the capsule is in the stomach and a second electrical signal when the capsule is in the small intestine. In particular embodiments, this is accomplished using an embodiment of the capsule having three electrodes positioned on its surface, the first and second electrodes being exposed and the third electrode covered by an insulative pH sensitive coating which remains in the stomach but degrades in the pH environment of the small intestine expose the third electrode when in the small intestine.

When the capsule reaches the stomach, the first and second electrode electrically couple to fluids in the stomach and the first electrical signal is generated and transmitted for detection and analysis by an external receiver unit or other device. At this point, the insulative coating over the third electrode is still intact. However, when the capsule reaches the small intestine the coating degrades to expose the third electrode which along with the second electrode electrically couples with the fluids in the small intestine to generate the second electrical signal which is transmitted. The first and second generated signals will typically be detected and analyzed by a receiver unit worn or otherwise in proximity to the patient. A gastric emptying parameter, such as GE time, is then determined using information from the first and second electrical signals. For gastric emptying time (GET)

this is done by subtracting the start time of the first signal from the start time of the second signal. This determination of GET can be done by logic resources resident on the external receiving device or the capsule. The respective signals including their start times can also be used to provide information on the location of the capsule including the location at a particular moment in time. For example, the start of the first signal provides information that the capsule has reached the stomach while the start of the second signal provides information that the capsule has reached the small intestine. The first and second signals can also be halted after a fixed interval, for example, about one to ten seconds in order to conserve power on the capsule including battery power. After the device enters the small intestine and the coating degrades, it then passes through the digestive tract and is eliminated in the feces. Also, while the coating degrades, the capsule shell does not and the capsule passes through the patient's intestinal tract intact. In some embodiments, the progress of the capsule can be monitored using ultrasound imaging or fluoroscopy. In use, this approach provides a verification of capsule location as determined from the first and second signals. Further, location information from imaging may be used to develop a model to correlate signal generation location information with a range of positions in the stomach or small intestine. Such a model may be used when doing subsequent GET tests without imaging to improve the accuracy of gastric emptying time calculation and calculation of other GE parameters as well. In additional or alternative embodiments, location information of the capsule may be determined using a combination of RF and acoustic signals (detected from three or more acoustic receivers placed on or near the patient's skin) to triangulate the position of the capsule at a moment in time indicated by an RF signal. Further description of apparatus, systems and methods for determination of capsule location using this approach may be found in one or more of U.S. Pat. Nos. 7,160,258, 8,005,536, 8,360,976, 8,617,070, 9,167,990 and 9,456,774 which are incorporated by reference in their entirety for all purposes.

In particular embodiments of the invention, the methods and results from measuring GE time or other GE parameter can be used to diagnose a patient's gastroparesis or other like condition causing slow reduced movement of food through the GI tract. GE time can be determined as described above and then the determined time can be compared to a range of values for normal gastric emptying time and those for Gastroparesis. A determination can then be made if the patient has Gastroparesis based on the comparison. In some embodiments, an algorithm for doing the comparison can reside in a controller or other logic resources of the external receiver unit or another computing device. Typically, the algorithm will be implemented by software by means of the GET module or a separate diagnostic module for performing Gastroparesis diagnosis. A number of GE tests can be run to improve the accuracy of the diagnosis particularly, if the patient is in the borderline region between normal GE times and those for Gastroparesis. The diagnostic module may also use artificial intelligence and/or self-learning routines to look at pools of patients and so improve the accuracy of diagnosis. It can also be used to assess the effectiveness of treatments for an individual patient's Gastroparesis by looking at reductions and/or trends in reductions in the patient's GE times over the course of treatment.

In related embodiments, GE times determined by embodiments of the invention can be used to help the patients with Gastroparesis or a related disorder know when and how much of a subsequent portion of food to eat after eating a first portion. In particular by knowing their gastric emptying time, patients can time the consumption and amount of a second or subsequent portion so they do not suffer from some of the adverse effects of Gastroparesis including nausea and vomiting since they will be allowing sufficient time for their stomach to empty before they eat their next portion. They can also use the GE time to control the size and nutritional content (e.g., fat, protein, carbohydrate etc.) of their initial portion as well since they know that fatty foods have longer residence times in the stomach so they can make adjustments accordingly in their subsequent portions. Algorithms, can be developed which use the patient's individual GE times, in particular those developed using embodiments of the test meal described herein (which have a known nutritional content) to make recommendations about timing, portion sizes and nutritional content of food to eat. The algorithm may be contained in a software module embedded in the controller/microprocessor of the external receiver unit described herein. The algorithm can be self-learning in that it can provide for input from the patient on symptomology they are experiencing (e.g. nausea) after eating meals of known nutritional content, portion size and time after a previous meal. The algorithm then uses the symptomology and meal information to tune or fine tune recommendations about portions sizes and timing between portions or meals.

In other embodiments, methods for measurement of GE times or other GE parameter can be incorporated into other medical uses. For example in one or more embodiment, measurement of GE time can be used to control administration of therapeutics agents to the patient, including adjustment of the dose and timing of administration. For the case of diabetics the measured GE times can be used to let them know when to administer a dose of insulin or other glucose regulating agent after a meal since they will have good idea based on the GE time when their blood glucose will rise after eating a meal. In use such, approaches helps diabetics to better control their blood glucose levels within normal range since they can now time their insulin injection based on when they eat a meal. GE time can also be used to titrate the dose and type of insulin or other glucose regulating agents. For example for slower times they may want to take a lower dose of insulin so that they do not become too hypoglycemic and vice versa (e.g., higher doses for faster GE-times so they do not become hyperglycemic). The recommended administration times can be incorporated into algorithms in software module of the receiving unit described herein. Other medications which can be so timed and adjusted include incretins such as various GLP-1 incretins including, for example Exenatide, available under the tradename BYETTA. Other factors which can be used in conjunction with GE times in adjusting or titrating the dose and timing of the glucose regulating compound can include the half-life of the particular glucose regulating agent. So, for example, such agents having shorter half-lives can be taken sooner after eating a meal than those with longer half-lives.

Further details of these and other embodiments and aspects of the invention are described more fully below, with reference to the attached drawing figures.

BRIEF DESCRIPTION OF THE DRAWINGS

Various embodiments of the present invention will now be discussed with reference to the appended drawings. It should be appreciated that the drawings depict only typical embodiments of the invention and are therefore not to be considered limiting in scope.

DETAILED DESCRIPTION OF THE INVENTION

Embodiments of the present invention provide devices, systems and methods for measuring a gastric emptying (GE) parameter (GEP), such as a gastric emptying time (GET). Particular embodiments provide a swallowable capsule 10 having three or more electrodes E (E1, E2 and E3) with one of the electrodes covered by an enteric or other coating which remains intact in the stomach but degrades in the small intestine (SI). The electrodes E are coupled to circuitry C such that when the capsule is in the stomach, current flow occurs between the first two electrodes generating a first signal. In the small intestine, current flow occurs between the second E2 and now uncovered third electrode and E3 generating a second signal. These two signals can be transmitted and analyzed externally or by an internal controller 60 to determine a GEP, e.g., a GET. The patient may wear an external device configured to receive and analyze the signals to determine GET. Additional electrodes E may be included for generating additional signals to provide information for determination of a GET or other GEP such as the transit time of the capsule through the small intestine. Embodiments of the invention may be used, for example, to diagnose gastroparesis and to provide patients with information on when to eat meals or administer insulin or other glucose regulating element after eating a meal.

Figure 1A:
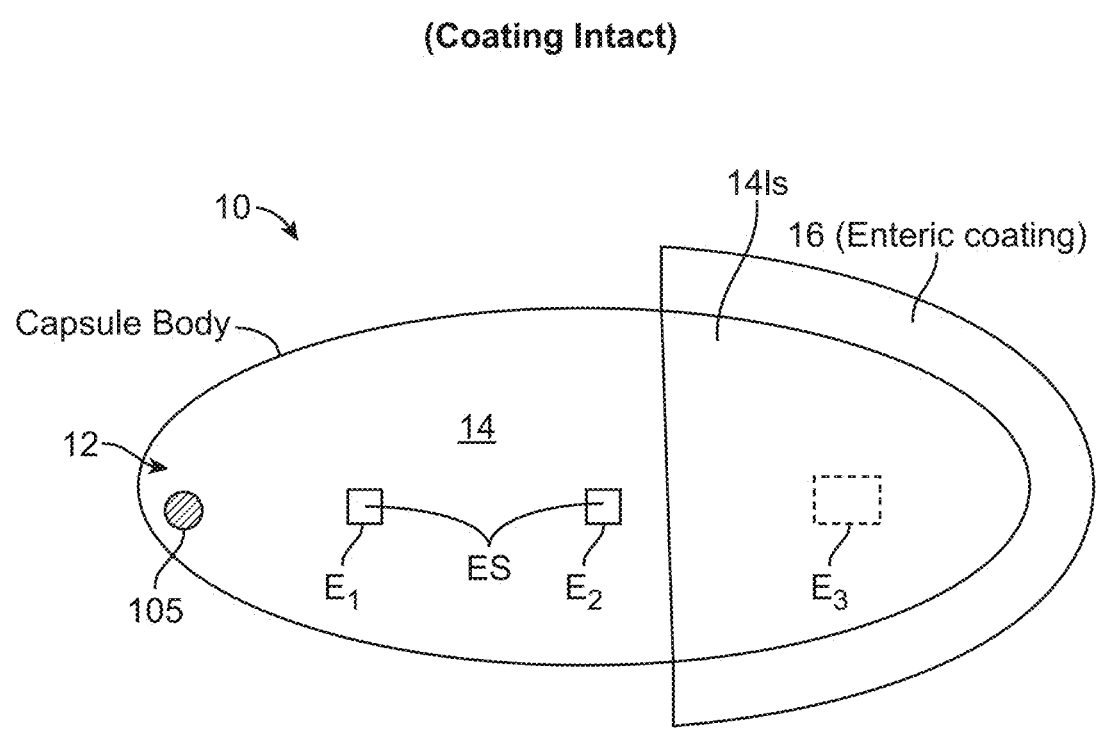
FIGS. 1A-1C illustrate different views and embodiments of the swallowable capsule of the present invention showing orientations of sensing electrodes and enteric coatings.
Figure 1B:
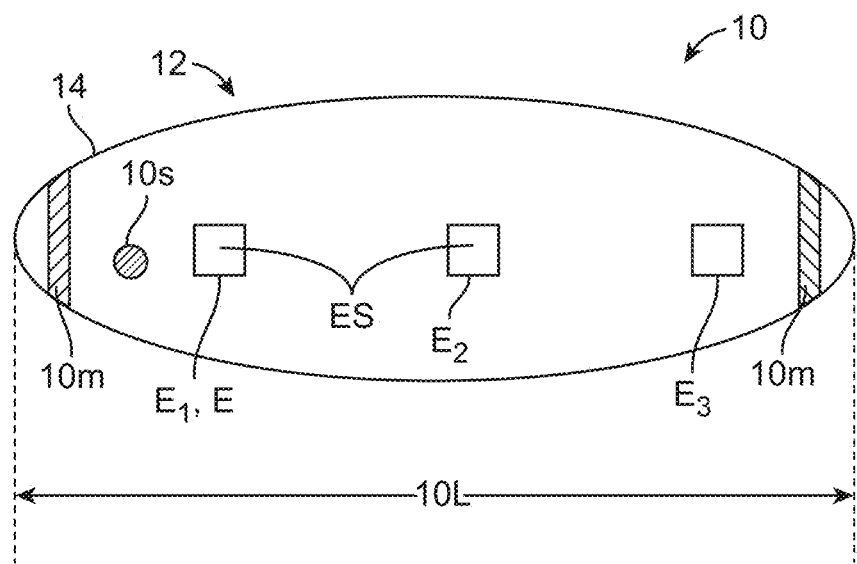
Figure 1C:
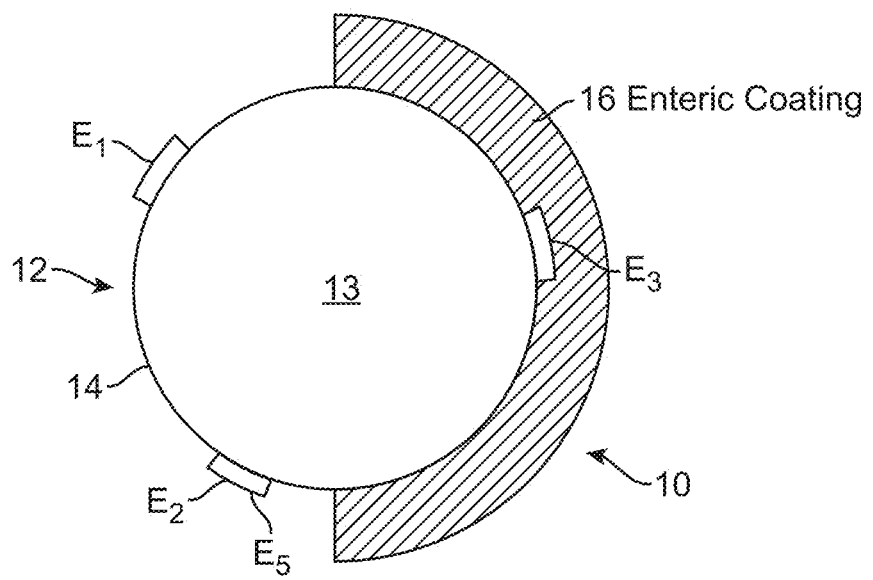

Referring now to the drawings, FIGS. 1A-1C illustrate different views and embodiments of the swallowable capsule 10 of the present invention showing orientations of sensing electrodes and enteric coatings. As shown in FIG. 1A, a swallowable capsule 10 comprises a capsule body 12 having an exterior surface 14 (also referred to herein as an outer body surface) defining a capsule interior 13. The capsule body may be fabricated from various biocompatible non toxic polymers known the in art which do not degrade in the stomach or other portion of the GI tract. The capsule body 12 is desirably sized to pass easily from the stomach to the small intestine during gastric emptying and doesn't stay in the stomach too long (e.g., hours). In various embodiments, the capsule size (when in oval or oval like shape) can be 00, 1, 2, 3, 4, or 5 according to a standard capsule chart. In preferred embodiments the capsule size is 4 or 5. Typically, capsule 10 will have an oval or oval like shape but other shapes are also contemplated including circular, semicircular, cylindrical, pyramidal and rectangular with rounded edges.

First, second, and third electrodes E1, E2, and E3 have conductive surfaces ES exposed on the exterior of the capsule body so that immersion of the capsule into an electrically conduce medium, such as the fluids present in a patient's stomach and/or intestines, will provide an electrically conductive bridge between the electrodes. At least one of the electrodes, and in some instances, two or three of the electrodes, will initially be covered by an electrically insulating cover, typically a coating 16, to electrically isolate pairs of the electrodes (e.g., E2 and E3). Desirably, the coating is configured to provide sufficient electrical resistance such that minimal or no current flows between E3 and other electrodes when the coating is in place. In particular embodiments the coating may be configured to provide over 1 mega ohm of resistance more preferably over 10 mega ohms of resistance between E3 and any other uncovered/uncoated electrode E.

The coating 16 or other cover is configured to selectively degrade in the presence of the stomach and/or intestinal fluids. In particular embodiments, the pH-sensitivity of the coating is configured so that it will remain intact when present in the stomach but degrade as the pH changes (e.g., increases) after the capsule passes through the pylorus into the small intestine. In this way, the coating 16 serves to selectively expose the third electrode E3 in the small intestine, allowing current to flow through circuit 2 and cause the generation of output signal S2 which is used to determine when the capsule is in the small intestine. Put in another way, the coating 16 together with circuits C1 and C2 function as a pH sensor for determination of when capsule is in the stomach, small intestine or location in the GI tract (e.g., the large intestine).

The coatings for used for coating 16 which remain intact in the stomach but are degraded in the small intestine are typically referred to as enteric coatings. In various embodiments, the enteric coating used for coating 16 may correspond to copolymers derived from esters of acrylic and methacrylic acid (e.g. methacrylic acid-ethyl acrylate copolymers) made under the trade mark EUDRAGIT (available from the EVONIK Industries AG). The particular EUDRAGIT coating selected may be selected to degrade at a selected pH in the small intestine (5.5 in the duodenum, 6.5-6.8 in the jejunum and 7-8 in the illeum). In particular embodiments, the EUDRAGIT coating is selected to degrade above a pH of about 6.5 to know that the capsule has fully entered the small intestine by being in the mid portion of the small intestine (e.g., the jejunum) before the third electrode E3 is exposed. According to additional or alternative embodiments, coating 16 may comprise multiple coatings 16 which are placed over one or more electrodes E and configured to degrade at a selected location in the small intestine. In use such embodiments allow for the determination of transit times through specific sections of the small intestine. For example, according to one embodiment, coating 16 may include a first coating configured to degrade at the pH at the entry of the duodenum (e.g., aground 5.5) exposing a third electrode (e.g. E3) and a second coating configured to degrade at the pH in the terminal ileum (around 7.5 to 8) exposing a fourth electrode allowing for a signal to be generated by a third circuit. The particular coating 16 as well as its thickness, can also be selected to have a known degradation time at or above a selected particular pH, for example 10 to 15 minutes. In use, such embodiments of coatings 16 having known degradation times improve accuracy of the GET measurement by taking this degradation time into account in the GET or other GE parameter calculation. In various embodiments, the thickness of coating 16 can be in a range from about 0.001 to 0.1 inches with specific embodiments of 0.005, 0.01, 0.025, 0.05, 0.075, 0.8 inches. The coating thickness can be selected based on one or more of the following: i) the amount of electrical resistance desired between covered and uncovered electrodes, ii) the degradation time of the coating in the small intestine or other GI tract location; and iii) the condition of the patient including their suspected degree of gastroparesis Thicker coatings 16 can be selected for patients having a greater degree of gastroparesis to provide a great amount of protection while the capsule is in the patient's stomach. Thicker coatings 16 can also be selected to provide increased amounts of electrical resistance between covered and uncovered electrodes. The electrical resistance of the coating 16 can also be increased through the use of biocompatible high resistance additives (e., those with a high dielectric constant) known in the art added to the methacrylic acid-ethyl acrylate copolymer or other coating.

As illustrated in the embodiment of FIG. 1A, electrode E3 is covered with the coating 16. After exposure to conditions within the smalls intestine, the coating will degrade, exposing E3 as shown in FIG. 1B. Thus, when the capsule 10 is initially swallowed and passes into the stomach, electrodes E1 and E2 will be exposed to the stomach liquids (e.g., acids) and will be in electrical contact (e.g., they will be electrically shorted) via conductive fluids in the stomach such as stomach acid and partially digested food. When the capsule 10 further passes into the intestines, the change in pH will degrade the coating and electrode E3 will then be shorted with both electrodes E1 and E2. As described in more detail below, this change of state in the electrical contact of the three electrodes will be used to generate signals that allow the timing of passage of the capsule between the stomach and the intestines to be tracked.

As shown in FIGS. 1A and 1B, the electrodes 1A-1C are distributed axially along the length 101 of the capsule and the coating covers one end of the capsule over electrode E3. FIG. 1C show an alternative arrangement where electrodes E1-E3 are distributed circumferentially over the exterior 14 of the capsule body 12 and the coating 16 covers one side or lateral surface 141s of the capsule exterior 14. The electrodes and the coating may be arranged in many other patterns, and more than three electrodes and more than one coating and/or one coating material may be employed. For example, all electrodes could initially be covered with a coating or other barrier which degrades within the stomach to expose a first pair of electrodes to confirm passage into the stomach. One or more additional electrodes E could be covered by one or more additional enteric coatings which degrade over different times and/or in different regions of the gastrointestinal tract, e.g., the large intestine in order to provide information on transit times of the capsule through a variety of locations in the GI tract. For example, two additional electrodes E positioned on the capsule body 12 could be covered by a second enteric coating which degrades in the large intestine in order to confirm passage of the capsule from the small intestine to the large intestine.

Figure 2A:
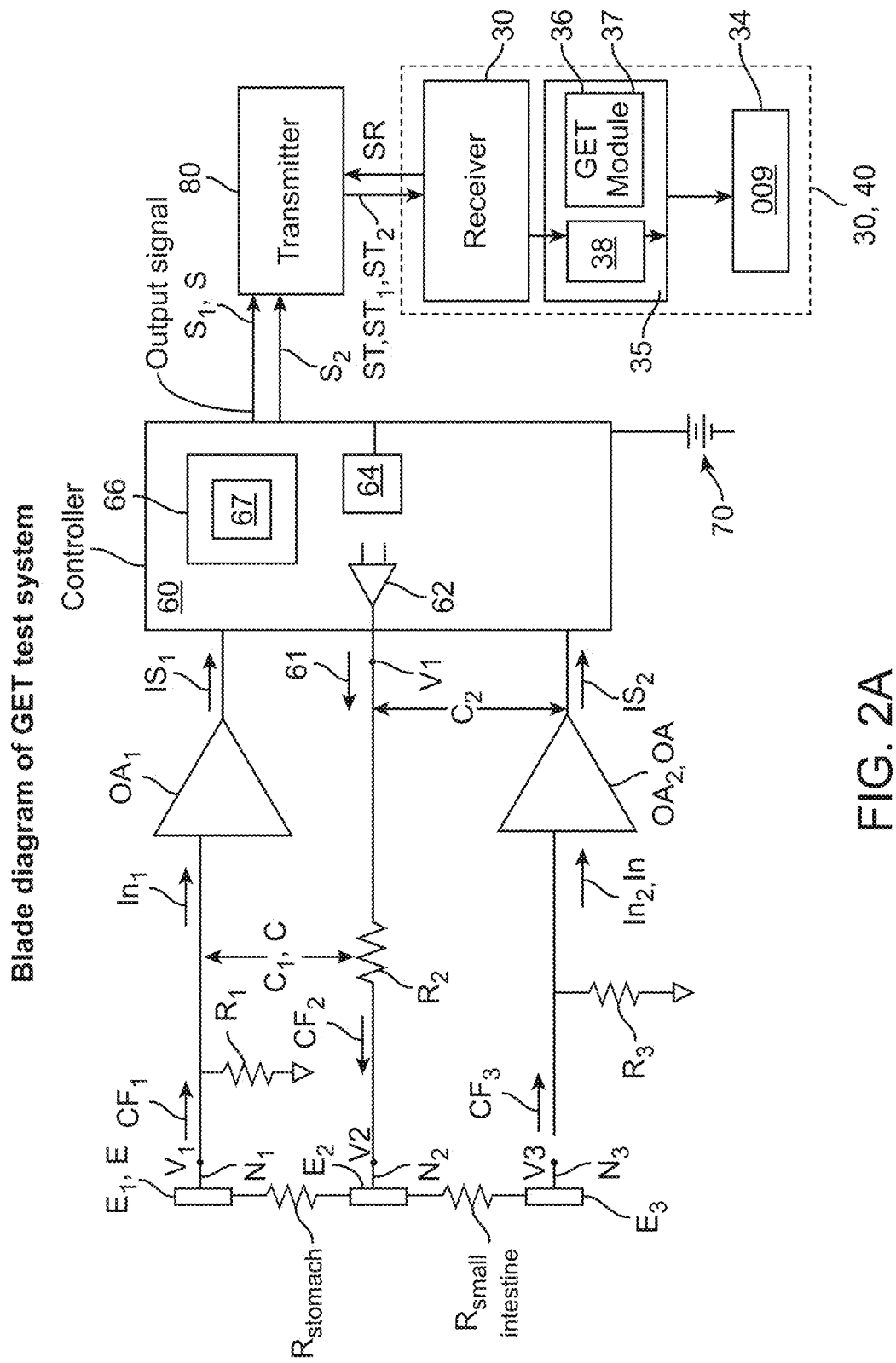
FIG. 2A is a block diagram of exemplary sensing and receiving circuitry useful in the devices and methods of the present invention.
Figure 2B:
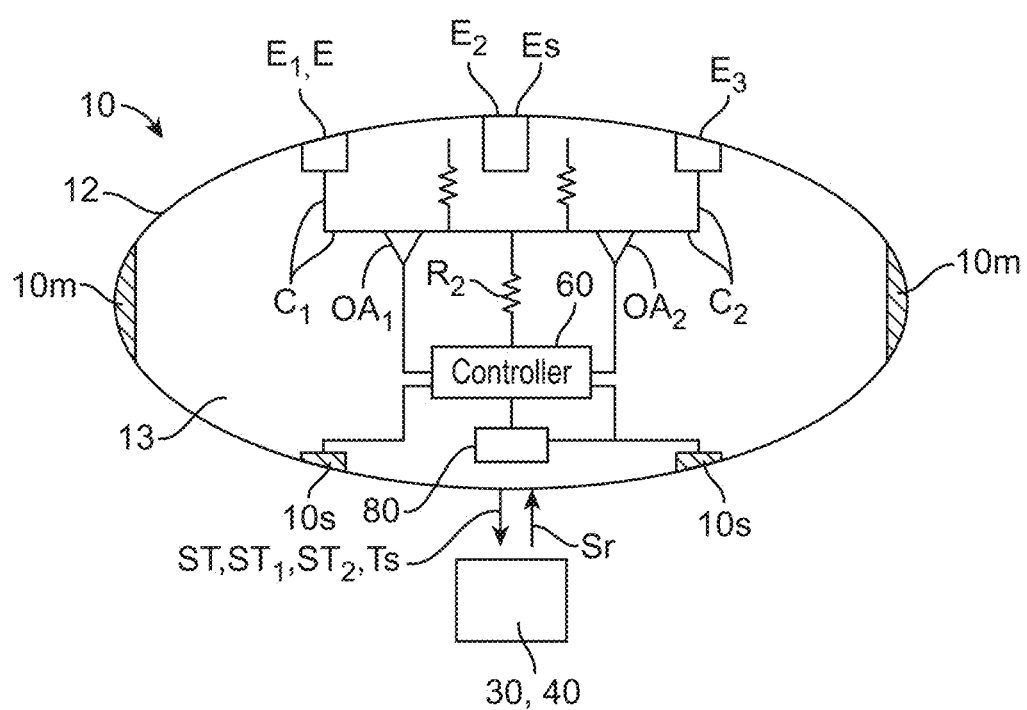
FIG. 2B illustrates an exemplary layout of the circuitry of FIG. 2A in an embodiment of the capsule.

FIGS. 2A and 2B, depict example circuitry or circuits C including circuits C1 and C2 for measuring GET or other GEB by detecting electrical shorting of the electrodes E1-E3. Typically, circuits C1 and C2 include an operational amplifier (opamp) OA, OA1 and OA2 respectively and at least three resistors R1, R2 and R3 respectively, which are desireably arranged in a voltage divider configuration, though other configurations contemplated. The opamp OA receives an input signal In from a node N of the respective circuit including the first or third electrodes E1 and E3, amplifies it and then sends the output signal as an input signal IS to the controller 60. So for example, opamp OA1 receives an input signal In1 from current flow CF1 from node N1, and opamp OA2 receives an input signal In2 from current flow CF3 from node N3. The voltages at each of the respective nodes N1, N2 and N3 are designated as V1, V2, and V3. The opamps OA1 and OA2 (or other opamp OC) may have gains from about 1 to 10,000 or larger, with specific embodiments of 100, 250, 500, 1000, 2500, 5000 and 7500. The gain can be selected based on the desired voltage of output signals S. Desirably, the resistances of R1 and R3 have a sufficiently high value so that no current enters the body from the capsule body 12 other than through the electrodes E. R2 also has a high value so that current entering the body through electrodes E is minimal. In various embodiments, the resistance of one more of R1, R2 and R3 have values greater than about 1 mega ohm and may be in a range from about 1 to 10 mega Ohm with higher values also contemplated. Resistors R1, R2 and R3 may be fixed or variable. In particular embodiments, the use of digital potentiometers is contemplated including for R2, where the resistance may be controlled by controller 60. The input voltage Vi for the circuits C1 and C2 is provided via a driver input signal 61 resulting in current flow CF2 to electrode E. According to one or more embodiments, driver signal 61 is provided by controller 60, e.g., by a signal generator or opamp 62 integral to controller 60 or other voltage source operably coupled to Node N2 and/or controller 60. One or both circuits of C1 and C2 may also include a capacitor (not shown) positioned in the circuit in a manner to ensure that current that flows between the electrodes in the stomach or small intestine is an AC current.

In various embodiments, circuits C1 and C2 or other circuitry C, can be configured to perform one or more functions used in determining a GET for a patient or other GE parameter. In particular embodiments, the first circuit C1 is configured to generate a first input signal IS1 when there is current flow between the first and second electrodes E1 and E2 and the second circuit C2 is configured to generate a second input signal IS2 based when there is current flow between the second and third electrodes E2 and E3. As is explained below, current flow occurs in the first circuit C1 when the first and second electrodes E1 and E2 come into contact with conductive fluids in the stomach such as stomach acids. When this happens, the first circuit C1 starts to generate an input signal IS1 (converted by the processor to a first output signal S1) which provides an indication of when the capsule 10 has reached the stomach after being swallowed. Similarly, current flows in the second circuit C2 after the insulative coating 16 degrades in the small intestine and the second and third electrodes E2 and E3 come into contact with conductive fluids in the small intestine. When this happens, the second circuit C2 generates an input signal IS2 (converted to a second output signal S2) which provides an indication of when the capsule 10 has reached the small intestine. Information from these two signals IS1 and IS2 (or their corresponding output signals S1 and S2), including their start times, can then be used to determine gastric emptying time or another gastric emptying parameter. In particular, the start time of the first input signal IS1 can be subtracted from the start time of the second signal IS2 to arrive at a gastric emptying time. Similar calculations can be done for output signals S1 and S2, which can be configured by processor 60 to have the virtually the same (e.g., within a few hundredths or thousands of a second or less) start times as input signal IS1 and IS2. In various embodiments, the calculation of GET (or other GE parameter) can be done by an external controller (e.g., a processor) or the controller 60 (e.g., processor) within capsule 10. According to one embodiment, the calculation is done by an external controller resident within an external receiver unit 30 (described herein) or another external device such as a cell phone, tablet, and the like. In this approach, software or other logic resident within the external controller uses the start times (or other information) of signals S1 and S2 (which are transmitted by the capsule) to perform the calculation of GET or other GE parameter. As is discussed below, signals S1 and S2 (or other output signal S) can be configured to be distinct (e.g., via distinct frequencies such as distinctive chirp signals described herein) so that they can be readily distinguished by software or other logic resident within the external receiver or other external device. In an additional or alternative embodiment, software or other logic resident within the controller on the capsule 10 can be configured to utilize the start time (or other information) of input signals IS1 and IS2 to make the calculation of GET or other GE parameter. In this approach, no distinction between the two signals is necessarily needed as the signals IS1 and IS2 may be inputted to the controller via separate input channels on the controller (e.g., via input channels on an A/D converter integral to or operatively coupled to the controller). In an alternative approach, the start times of IS1 and IS2 can be stored in memory on board capsule 10 (e.g., RAM, DRAM, etc. integral or coupled to controller 60) and then be transmitted to receiver unit 30 for processing by unit 30 or an external device 40 to calculate GET or other GE parameter.

In particular approaches for calculation of GET, allowances can be made for the estimated time it takes for the enteric coating 16 to degrade in the small intestine (e.g., 10 to 15 minutes), as well as other factors (e.g., whether the capsule is taken with food, as well as the age, weight and size of the patient and/or other medications which may slow gastric emptying e.g., opiodes, calcium channel blockers or anti diarrhea drugs). Such allowances can be incorporated into a software module (such as modules 37 or 67 described below) or other logic for determination of gastric emptying time which may be resident on a controller of an external device 40 or controller 60 in the capsule 10.

A discussion will now be presented on various aspects of controller 60. According to one or more embodiments, controller 60 may correspond to a microprocessor, an analogue device, a state device, or other logic resources known in the art. For embodiments where controller 60 corresponds to a microprocessor or other like device it will usually include one or more software modules 66, herein modules 66 including electronic instruction sets for performing one or more functions of the controller.

The controller 60 is operably coupled to circuitry C including one or both of circuits C1 and C2 so that it may receive input signals IS1 and IS2. It is also operably coupled to a power source 70 such as a lithium ion or other miniature chemical storage battery known in the art. In alternative embodiments, the use of micro super capacitors is also contemplated. It may also include or be operably coupled to a transmitter 80 such as an RF transmitter, for transmitting signals ST encoding information from the controller, to a receiver on an external device (e.g. receiver unit 30 or external device 40). In particular embodiments, transmitter 80 may transmit signals ST1 and ST2 encoding information on signals S1 and S2. In some embodiments, the controller 60 may include a low power RF generator and the transmitter 80 may correspond to a power amplifier which amplifies the low power RF signal coming from the controller. According to some embodiments, transmitter 80 may also correspond to a receiver which may receive signals Sr from unit 30 or device 40.

Controller 60 may be configured to perform a number functions either via hardware or software related to the determination of GET or other GE parameter. In particular, controller 60 may be configured to generate and/or utilize a clock signal 64 for determining the start times of the first and second input signals IS1 and IS2 so as to determine GET or other GE parameter. The clock signal may be single phase or multiphase (e.g., two phase or four phase). For embodiments where the controller comprises a microprocessor can be generated by a clock signal generator 65. According to other embodiments the clock signal can be generated by an analogue to digital converter which is integral to or operably coupled to controller 60. As discussed above, in one or more embodiments controller 60 will also typically be configured to generate or otherwise provide a driver signal 61 sent to the second electrode E2 and receive signals IS1 and IS2 from the first and second circuits when current is flowing through them in the stomach and/or small intestine. Generation of drive signal 61 can be done by software and/or hardware by a driver amplifier/generator 62 integral or otherwise operably coupled to controller 60. Typically, the driver signal 61 is in the form of an AC voltage with low amperage in the milliamp range (e.g., 1-20), more preferably in the microamp range (0.5 to 1 µa) and voltage in the range from 0.5 to 2 volts with other ranges contemplated. Controller 60 is further configured to generate a first output signal S1 in response to the first input signal IS1 from the first circuit and a second output signal S2 in response to the second input signal IS2 from the second circuit. The respective output signals will typically be in AC form and configured for transmission by the RF or other transmitter 80 integral to or otherwise coupled to the controller. These signals may be generated by the controller itself or a signal generator electrically coupled to the controller. In particular embodiments, the output signals such as S1 and S2 may correspond to distinctive chirp signals SC known in the signal processing arts including first and second chirp signals SC1 and SC2. In one particular embodiment, the first output signal may correspond to an up chirp signal SCU and the second signal to a down chirp signal SCD, the up chirp signal having a higher frequency then the down chirp signal. The controller can also control how long a respective output signal is generated once it starts. For example, it can stop the first output signal S1 after a selected period of time after that signal starts. It may also do the same for the second output signal. The time periods, which may be in the range of 1 to 20 seconds, more particularly 1 to 10 seconds, are selected to provide sufficient time for detection and recording by an outside receiver (e.g., receiver unit 30 described herein) 60 or the controller itself, as well as to conserve battery power.

In one or more embodiments the controller 60 may also be configured to generate and transmit a tracking signal TS so as to know when the capsule has been excreted from the patient's GI tract. Activation of the tracking signal may be based on detection of either input of signals IS1 or IS2, with the tracking signal initiated at detection of the input signals or a select time period afterwards. The receiver unit 30 and/or external device 40 can be configured to detect the tracking signal and provide status updates to the patient of detection or no detection of the tracking signal. In particular embodiments, unit 30 and/or external device 40 can be programmed or otherwise configured to provide an alert to the patient of when capsule the capsule has been excreted based on failure to detect the tracking signal for predetermined period of time (e.g., 5 to 10 minutes or longer). Unit 30 and/or external device can also be programmed to use detection of the tracking signal to alert the patient after that the capsule has remained in their GI tract an undesirable amount of time (e.g., longer than 24 hours). The patient may then inform their doctor or take appropriate medication such as a laxative. In alternative or additional embodiments, capsule 10 may include radio-opaque or echogenic markers 10m in order to facilitate detection of the capsule in the GI tract by fluoroscopy, ultrasound or other medical imaging modality.

As discussed herein, controller 60 may also include programming or other logic in hardware or software for recording and storing the start time on the first and second input signals IS1 and IS2 well as other information such as their amplitudes. Signals encoding this data can then be transmitted to an external device by transmitter 80. The controller 60 may further include logic in hardware or software for calculating and analyzing gastric emptying times (GET) or other GE parameter using approaches described herein. For software implementations, the logic may be in the form of a software module 67, herein module 67 resident in the controller (e.g., in RAM, DRAM, ROM, flash or other memory. Module 67 is also referred to herein as a GET module 67. The same module 67 (or one similar to it), may also be resident in the controller 35 of external receiver unit 30 worn by the patient as is described below. In addition to calculation of GET by the subtraction method described above, module 67 (as well as module 37) may include algorithms for calculation of a GET which take into account other factors such as how long it takes for the enteric coating to dissolve as well as the amount, type and time of any food eaten before, during or after the capsule was ingested. This information can be used to make allowances for longer or shorter gastric empting times for the type and amount of food eaten. For example, liquid vs solid meals and protein rich foods which leave the stomach sooner than foods high in carbohydrates, while food high in lipids (e.g., fat) take the longest to leave the stomach. In some embodiments, including those where GET calculation is done by a controller on an external device 40 (e.g., a cell phone, tablet or other portable computation device known in the art), the patient may enter this information including the nutritional information and portion size into the external device. Controller 60, including module 67, may also include programming or other logic for calculation of other GE parameters including one or more of the following: GE velocity, the speed at which food/stomach contents moves from the stomach to the small intestine; average GE velocity, peak GE velocity, GET peristaltic contraction ratio, the ratio of GE time per number of peristaltic contractions; and GET average peristaltic force ratio, the ratio of GET time per average force of peristaltic contraction occurring prior to or during the transit of food from the stomach to the small intestine.

In additional or alternative embodiments described below with respect to FIGS. 6a and 6b, a specific procedure can be followed by the patient where the patient is given a test kit 50 (herein at GET test kit) containing a capsule 10 and a matched prepackaged GET test meal 52 having known a known portion size and known amounts of carbohydrates, protein, fat etc. The portion size and nutrition information of the test meal comprise what is described herein as test meal information. The test meal information may be pre-entered into an embodiment of the GET module which for test meal embodiments will typically be resident on capsule controller 60 (but may also be resident on the receiver unit controller 35). The patient is also instructed to eat the meal with the capsule or at a set interval before or after ingestion of the capsule. In some embodiments, the capsule may actually be embedded or otherwise surrounded by the test meal, ensuring that both are taken concurrently for embodiments where that is the desired approach. Embodiments using such a GET test kit 50 provide the benefit of reduced variability in gastric emptying due to the patient's eating habits and thus a more accurate result for GET or other GE parameter.

Figure 3:
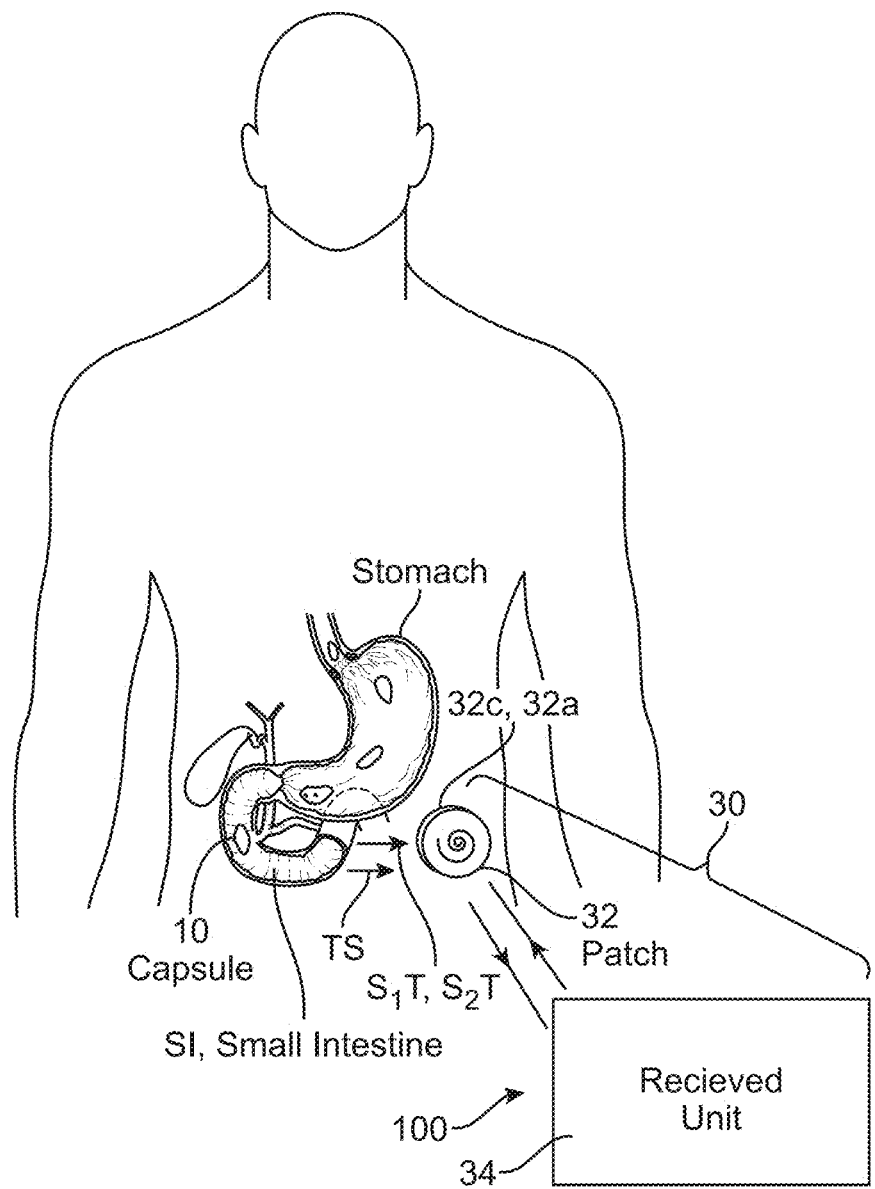
FIG. 3 illustrates external placement of a sensing patch on a patient's abdomen in order to detect passage of a swallowable capsule of the present invention from the patient's stomach into the small intestine.

Referring now to FIG. 3, a receiver unit 30 for receiving signals transmitted by capsule 10 encoding information on GET or other GE parameter may comprise and communicate with an adhesive patch 32 worn by the patient (for example, over the abdominal area) to facilitate communication between the receiver and the capsule. Collectively, capsule 10, receiver unit 30 and patch 32 comprise a system 100 for measurement of GET or other GE parameter. Receiver unit 30 may be incorporated into the patch or may be external to it and in communication with circuitry carried by the patch to receive signals from capsule 10. According to one embodiment where the receiver unit is external to the patch, patch 32 carries the circuitry necessary to receive signals emitted by the capsule 10 and then transmits those signal to receiver unit 30 which carries the software application or other programming necessary to receive, process and optionally further transmit data to the cloud, physician, or elsewhere. Receiver unit 30 will typically include a receiver 33, display 34, and a controller 35. Receiver 33 may correspond to an RF or other receiver known in the medical electronic arts. Controller 35 may correspond to a microprocessor which may include (or have electronic access to) one or more software modules 36 (herein modules 36) having logic for performing one or more operations including one or more of receiving, processing and transmitting signals S received from capsule 10 (e.g., signals S1 and S2). In particular embodiments, modules 36 include a GET module 37 which has logic for calculating GET or other GE parameter (e.g., small intestine transit time) The controller 35 may also include a timer device 38 (in hardware or software) for timing the receipt of signals S1 and S2 or other signal received from capsule 20. In particular embodiments, timer device 38 may correspond to a clock generator.

Patch 32 desirably corresponds to an adhesive patch configured to be worn over and adhere to the abdominal area of the patient so as to receive signals S1 and S2 or signal from capsule 10. The patch 32 may contain just the receiver unit 30 or other components as well. For example, according to one embodiment, all or a portion of the patch 32 may comprise a conductive material 32C arranged as an antenna to improve the reception of signals (e.g., S1 and S2) from capsule 10. Desirably, patch 32 is sufficiently flexible to bend and flex with movement of the patients abdomen and stay adhered to the skin (with device 30 attached) so as to able to be able detect signals from the capsule 10 even when the patient is active or otherwise changes positions. This can be achieved by fabricating patch 32 from elastomeric polymers and skin adhesives known in the medical device and polymer arts. Also the patch can be custom sized for a given patients abdomen (e.g., using 3rd printing methods) to further improve adherence. Patch 32 including receiver unit 30 may also be configured to wirelessly communicate (e.g. by a BLUETOOTH protocol described with another external communications device 40 such as a tablet device or smart phone which receives information (e.g., information contained in the first or second signals) from the patch and performs various computations to determine GE time or other GE parameter. While the capsule could communicate directly with the communication device 40, use of the patch 32 provides the benefit of improved signal receipt by device 30 (due to proximity) while still allowing the patient to easily see displayed GE times and enter information, e.g., meal content and times on the communication device onto the external.

Figure 4A:
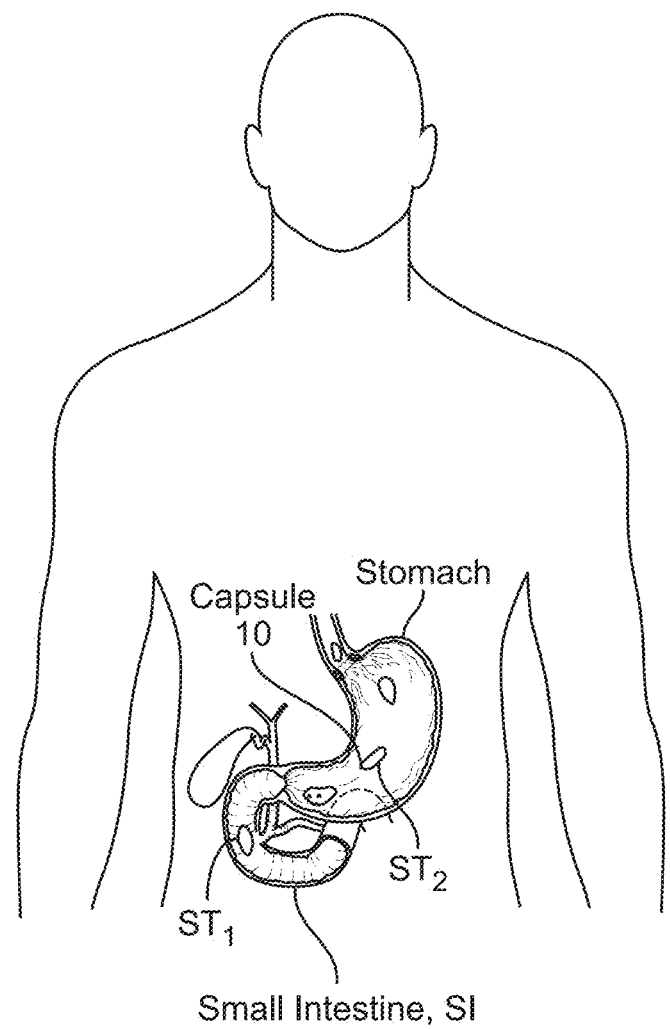
FIGS. 4A and 4B illustrate the progression of a swallowable capsule of the present invention through the patient's stomach into the small intestines beyond the duodenum.
Figure 4B:
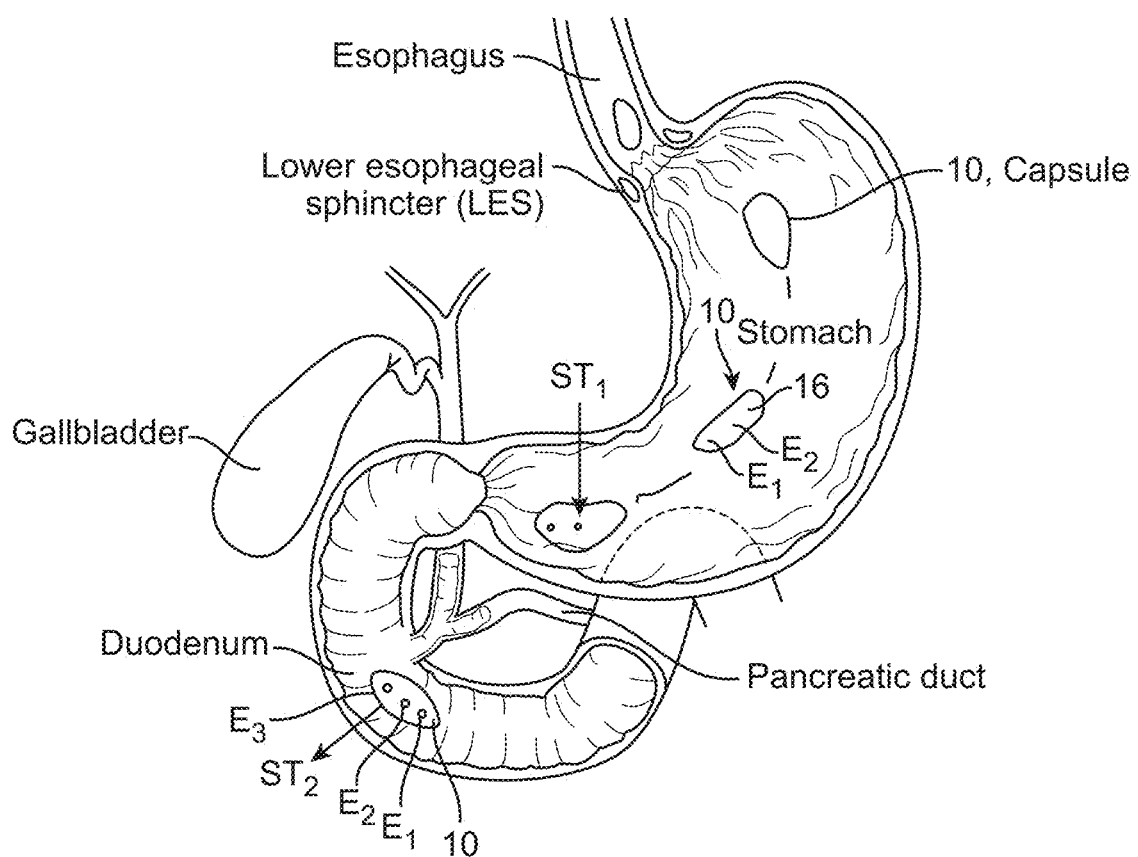

Referring now to FIGS. 4A and 4B, an embodiment of a method of using the capsule 10 to measure GET (or other GE parameter) will now be illustrated. After the patient swallows an embodiment of capsule 10 it passes from the esophagus into the stomach. Once there the stomach contents (e.g acids) provide a conductive pathway between the first and second electrodes E1 and E2 so there is current flow in the first circuit. This results in the generation and transmission of the S1 output signal. At this point, the insulative coating 16 over the third electrode E3 is still intact and there is no current flow in the second circuit and no generation of the S2 output signal. However, when capsule 10 reaches the small intestine, coating 16 degrades to expose the third electrode E3 which along with the second electrode electrically couples with the conductive fluids in the small intestine resulting in the current flow in the second circuit and the generation and transmission of the S2 output signal After passage out of the small intestine, the capsule enters the large intestine and is excreted out of the patient's body. In embodiments employing a tracking signal described herein, excretion of the capsule may be determined by loss of detection of the tracking signal TS by receiver unit 30. In embodiments having additional coatings 16 and electrodes E, additional output signals may be generated when the capsule reaches another selected location in the GI tract, such as the large intestine or the ileum portion of the small intestine. The patient may repeat the above procedure multiple times after excretion of a prior capsule in order to have multiple determinations of GET so as provide the physician with precision and other statistical metrics of a GET measurement. In particular the patient may take the pill at the same or different times over the day as well with or without food to account for affects due to circadian rhythm and diet. The patient may also repeat the above GET measurement procedure after a gastroparesis treatment has begun (e.g., the use of drugs or the implantation of a gastric pacemaker known in the art) in order to assess treatment efficacy and target endpoints as well as titrate the dosage of a drug or other therapeutic agent. The described GET measurement method may also be performed concurrently or nearly currently with a traditional GET measurement procedure (e.g. by swallowing a contrast agent and performing fluoroscopy) in order to provide a comparison between the two methods and if necessary calibrate the measurements made using the described methods to those of the traditional methods. According some embodiment the calibration can be done via software using one or more embodiments of the GET software module (e.g., modules 37 or 67).

Figure 5:
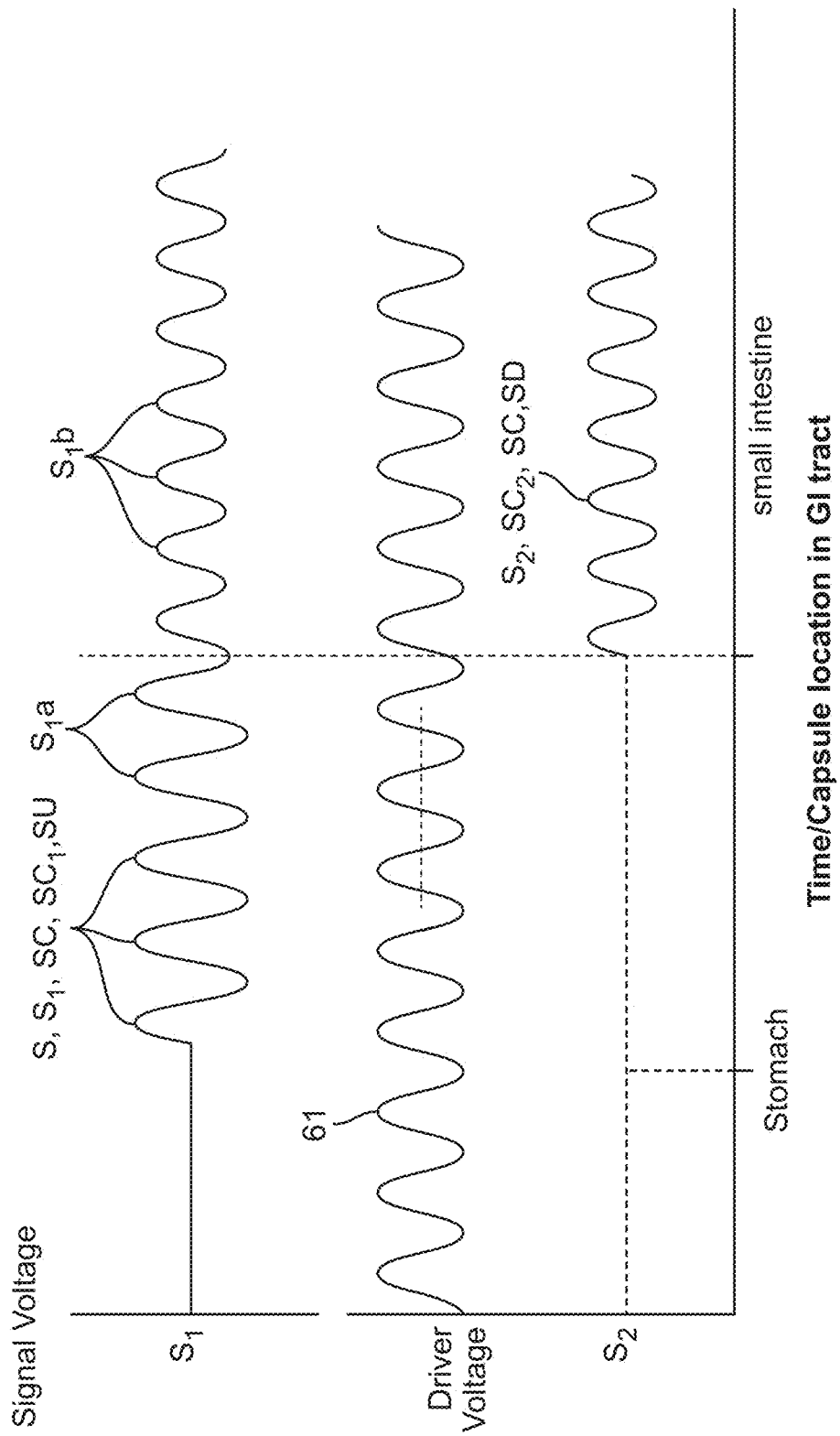
FIG. 5 illustrates the output signals and driver voltage produced by the circuitry of FIGS. 2A and 2B.

Referring now to FIG. 5, a discussion will be presented of the signals and functions of the circuitry of the embodiments of FIGS. 2A and 2B. As discussed herein, the circuitry typically includes a controller 60 which among other functions generates or processes one or more of the signals in circuitry C including circuits C1 and C2. In various embodiments, it may be configured to generate a driver signal 61, sent to the second electrode E2 and receive signals (e.g., input signals IS1 and IS2) from the first and second circuits C1 and C2 when current is flowing through them. Typically, the driver signal 61 is in the form of an AC voltage with very low amperage in the milliamp range (e.g., 1-20 milliamps) and voltage in the range from 0.5 to 2 volts with other ranges contemplated. Controller 60 is further configured to generate a first output signal S1 in response to the first input signal IS1 from the first circuit and a second output signal S2 in response to the second output signal from the second circuit. The respective output signals S1 and S2 will typically be in AC form and configured for transmission by the RF or other transmitter (e.g., acoustic) integral to or otherwise coupled to the controller. Desirably, the first and second output signals S1 and S2 are configured to have distinct frequencies (or other waveform characteristic) to facilitate their individual detection, e.g., by the receiver unit 30 or like device. According to one or more embodiments signals S1 and S2 are configured as chirp signals SC known in the electronic and signal processing arts. In one particular embodiment, the first output signal S1 may correspond to an up chirp signal SU (in which the frequency increases) and the second signal S2 a down chirp signal (in which the frequency decreases). These signals may be generated by controller 60 itself or a signal generator electrically coupled to the controller.

In addition to use of distinctive chirp signals, other means are contemplated for determining when capsule 10 has reached the small intestine. For example as shown in FIG. 6, S1 will typically decrease in amplitude once the capsule reaches the small intestine due to the voltage divider arrangement of electrodes E1, E2 and E3. This decrease is specifically illustrated by the decrease in amplitude going from section S1$a$ to section S1$b$ of the S1 waveform shown in FIG. 6. As such, controller 35 on unit 30 or a controller on external device 40 or controller 60 can be configured to detect the decrease. The controller 60 may also control how long a respective output signal is generated once it starts. For example, it can stop the first output signal S1 after a selected period of time after that signal starts. It may also do the same for the second output signal. The time periods, which may be in the range of about 1 to 10 seconds, are selected to provide sufficient time for detection and recording by communication device 30 or the controller itself. In particular embodiments, the first output signal is stopped soon after initial detection by the receiver unit 30 in order to facilitate detection of the initiation of the second output signal, e.g., so there is no possible confusion between the two signals by unit 30 or external communication device 40.

Figures 6A, 6B:
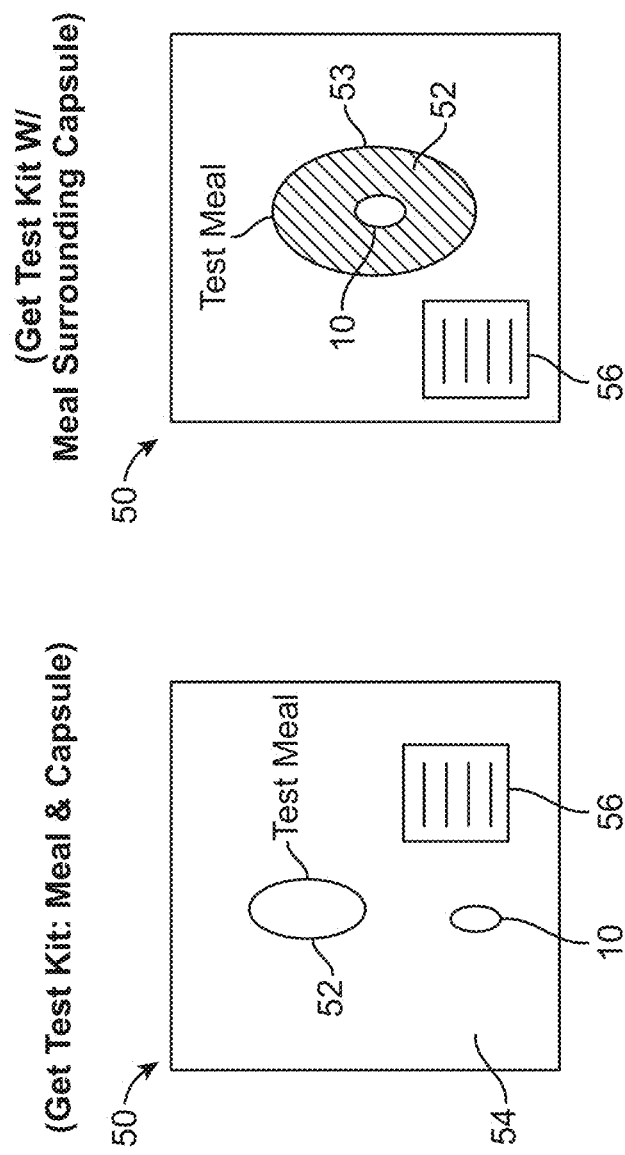
FIGS. 6A and 6B illustrate embodiments of test kits for establishing a baseline gastric emptying time (GET) for individual patients.

Referring now to FIGS. 6A and 6B, in one or more embodiments of the invention a test kit may utilized for establishing a baseline gastric emptying time (GET) for individual patients. Baseline GET being that where the patient eats a fixed quantity of food having known a nutritional content (e.g. a known amount of fat, protein carbohydrates, herein referred to as nutritional information) to reduce variability in GETs occurring for different meal nutritional content and meal size. Collectively, this information is referred to as nutritional information. According to one embodiment, a GET test kit 50 may include the capsule 10 and a matched prepackaged GET test meal 52 having a known portion size known amounts of carbohydrates, protein, fat etc., typically in a sterile pack or package 54. These and other parameters and characteristics of the test meal are known as test meal information. Such test meal information may be pre-entered into the GET module resident on the controller of the capsule 10, receiver device 30 or an external device 40. The test meal information may then be used to adjust the final determined value for GET accordingly. For example, GE times can be decreased for higher protein and/or denser meals which may take more take to travel from the stomach to the small intestine. The reverse being the case for less dense and/or low protein content meals. The kits will typically also include instructions 56 for the patient to eat the meal with the capsule or at a set interval before or after ingestion of capsule 10. As shown in FIG. 6B, in an alternative embodiment, the capsule 10 may actually be embedded or otherwise surrounded by the test meal 52 so as to compromise a capsule embedded test meal 53. Embodiments of such a capsule embedded test meal 53 ensuring that the both are taken concurrently for embodiments where that is the desired approach. In either case, embodiments using a GET test kit 50 including a test meal provide the benefit of reduced variability in GET or other GE parameter measurement due to the patient's eating habits and thus provide a more accurate and reproducible result for GET or other desired GE parameter.

In various embodiments, the physical properties of capsule 10 can be configured to facilitate passage of the capsule through the stomach in the same manner and/or at the same rate as food so as to more accurately predict GET or other GE parameter. For example, according to one or more embodiments, the density of the capsule may be configured to approximate that of typical stomach contents with food present which is approximately 1 gr/cc (per the article by M J Ferrua et al., referenced below. When capsule 10 has such a density, the capsule neither floats at the top nor sinks to the bottom of the stomach when it contains food. Rather, it passes through the stomach in the same manner and at the same rate as digested or partially digested food. Also, if taken with food, the capsule will pass through the stomach along with the bulk of the digested food contents (also in the stomach) and in the same time interval as the food contents. In use, embodiments of the invention having a capsule so configured provide the benefit of a more accurate measurement of gastric emptying time or other gastric emptying parameter for digested food since the capsule mimics the density of digested food in the stomach. A range of capsule densities is also contemplated for example 0.5 to 1.5 mg/cc, with higher or lower density selected depending upon the condition of patient and/or the size and contents of a test meal (described below) taken along with capsule. Obtaining a specific capsule density can be achieved by selection of the capsule body materials as wells as the components and filler material placed in the capsule body. The filler material may comprise various biocompatible polymeric material known in the art including polymer gels.

In particular embodiments, the density of the capsule can be matched to that of the composition/content of the test meal. So for example, higher densities (e.g. >1.0 ml/cc, 1.1 to 1.5 ml/cc) for the capsule may be used with more dense test meals (e.g., those containing more protein) and lower densities (e.g. <1.0 ml/cc, 0.5 to 0.9 ml/cc) may be used for less dense test meals (e.g. bread), and moderate (e.g., 1 densities may be used for moderate dense meals which approximate the density of water, e.g., milk shakes soup etc. Further information on the densities of stomach contents as well as the motility pattern and velocity profiles and patterns within the stomach including the pylorus may be found in the article by M J Ferrua et al. entitled, *Modeling the Fluid Dynamics in a Human Stomach to Gain Insight of Food Digestion*, Food Sci. 2010 September; 75(7): R151-R162, which is incorporated by reference herein for all purposes.

Figure 7:
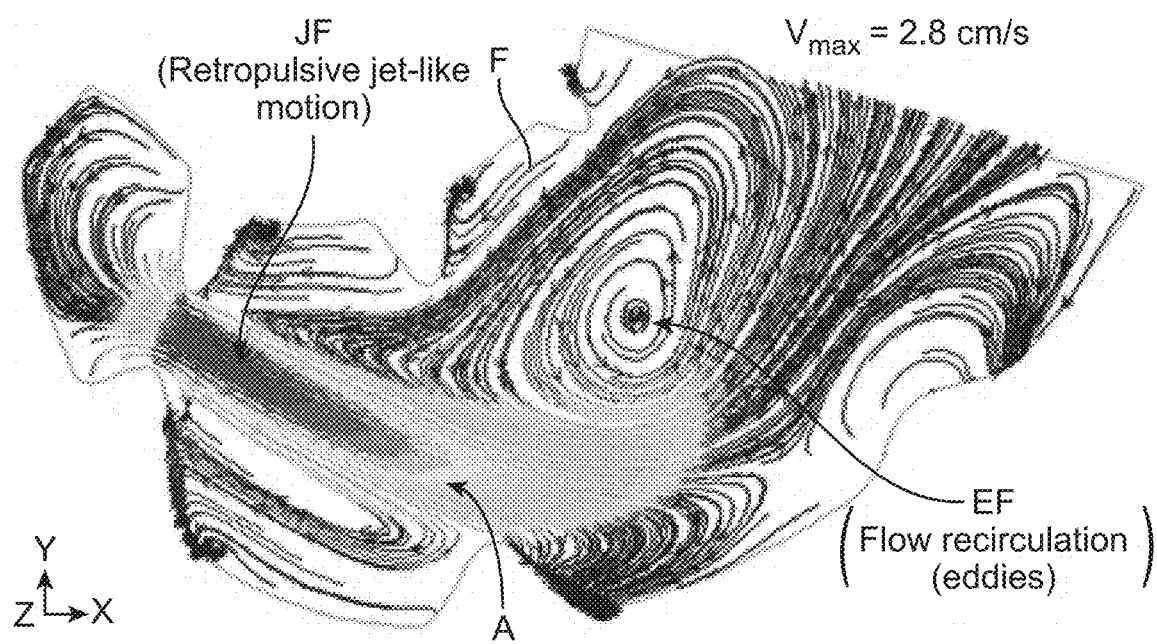
FIG. 7 is a graph of velocity streamlines within the stomach illustrating the velocity fields within different areas of the stomach resulting from peristaltic contraction of the stomach including a flow circulation (eddy) field in the corpus and a jet field in the antrum area of the stomach.

In other embodiments, the shape of the capsule can be selected for the particular velocity field or profile within particular portions of the stomach such that capsule is advanced or remains within that portion for period of time before being advanced. Referring now to FIG. 7, as known in the art (e.g., the paper by Ferrua et al.) there are two velocity fields created in the stomach by peristaltic motion these include a recirculation or eddy field (EF) in the Corpus portion C of the stomach which is low velocity and a high velocity or jet field (JF), also described as a retro-pulsive jet field, in the stomach antrum portion A of the stomach. Accordingly, in one embodiment an elongated shaped capsule (e.g., oval, cylindrical etc.) can be used so that the capsule is readily picked up and transported from the eddy field to the retro-pulsive jet field. Alternatively in another embodiment, a spherical shaped capsule can be employed when it is desired the capsule remain in the eddy field for longer periods of time. Other shapes are also contemplated to facilitate retention in the eddy field or transfer of the capsule between from the eddy field to the retro-pulsive jet field.

In still other embodiments, the surface tension of the outer surface of capsule 12 body can configured to be in the same range as that of the gastric juices/liquid content of the stomach such that the gastric juices readily wet the surface of the capsule body. In various embodiments this surface tension (i.e., the air liquid surface tension can range from about 30 to about 45 dynes/cm with a specific values of 30.5, 33, 35, 36.8 38, 40, 42, 43 and 44 dynes/cm. For embodiments where the capsule is taken with food such as with test meal 52 the capsule body can have a surface tension in the range of about 28 to 32 dynes/cm with specific values of 30 and 30.5 and 31 dynes/com. Approaches for obtaining such surface tensions can include the use of biocompatible polymers and polymeric coatings known in the art having the desired surface tension. For example in one or more embodiments capsule body 12 may comprise one or more forms of polyethylene which has surface tensions in the range of 35 to 36 dynes/cm or polyethylene teraphalate which has surface tension of about 42 dynes/cm. Other approaches may include the use of surface treatments such as various plasma treatment and other chemical treatments known in the polymer and surface treatment arts.

In use, such embodiments of capsule body 10 having one of the aforementioned surface tensions, allow for the capsule 10 to be readily carried by and flow with the liquid digested contents of the stomach as they are propelled and otherwise move through the stomach from peristaltic contraction or other related digestive motion. This in turn, allows movement of the capsule through the stomach to more accurately reflect the movement of digested liquid food contents through the stomach providing for more accurate measurement of GE time or other GE parameter.

Method for Diagnosis of Gastroparesis

In various embodiments of the invention, results from measuring GE time or other GE parameter obtained from using embodiments of swallowable capsule 10 can be used to diagnose a patient's gastroparesis or other like condition causing slow reduced movement of food through the GI tract. GE time can be determined as described above and then the determined time can be compared to a range of values for normal gastric emptying time and those for Gastroparesis. A determination can then be made if the patient has Gastroparesis based on the comparison. In some embodiments, an algorithm for doing the comparison can reside in a controller or other logic resources of the external receiver unit or another computing device. Typically, the algorithm will be implemented by software by means of the GET module or a separate diagnostic module for performing Gastroparesis diagnosis. A number of GE tests can be run to improve the accuracy of the diagnosis particularly, if the patient is in the borderline region between normal GE times and those for Gastroparesis. The diagnostic module may also use artificial intelligence and/or self-learning routines to look at pools of patients and so improve the accuracy of diagnosis. It can also be used to assess the effectiveness of treatments for an individual patient's Gastroparesis by looking at reductions and/or trends in reductions in the patient's GE times over the course of treatment.

Use of Gastric Emptying Time for Timing of Meal Consumption

In related embodiments, GE times determined by embodiments of the invention can be used to help the patients with Gastroparesis or a related disorder know when and how much of a subsequent portion of food to eat after eating a first portion. In particular by knowing their gastric emptying time, patients can time the consumption and amount of a second or subsequent portion so they do not suffer from some of the adverse effects of Gastroparesis including nausea and vomiting since they will be allowing sufficient time for their stomach to empty before they eat their next portion. They can also use the GE time to control the size and nutritional content (e.g., fat, protein, carbohydrate etc.) of their initial portion as well since they know that fatty foods have longer residence times in the stomach so they can make adjustments accordingly in their subsequent portions. Algorithms, can be developed which use the patient's individual GE times, in particular those developed using embodiments of the test meal described herein (which have a known nutritional content) to make recommendations about timing, portion sizes and nutritional content of food to eat. The algorithm may be contained in a software module embedded in the controller/microprocessor of the external receiver unit described herein. The algorithm can be self-learning in that it can provide for input from the patient on symptomology they are experiencing (e.g. nausea) after eating meals of known nutritional content, portion size and time after a previous meal. The algorithm then uses the symptomology and meal information to tune or fine tune recommendations about portions sizes and timing between portions or meals.

In other embodiments, methods for measurement of GE times or other GE parameter can be incorporated into other medical uses. For example in one or more embodiment, measurement of GE time can be used to control administration of therapeutics agents to the patient, including adjustment of the dose and timing of administration. For the case of diabetics the measured GE times can be used to let them know when to administer a dose of insulin or other glucose regulating agent after a meal since they will have good idea based on the GE time when their blood glucose will rise after eating a meal. In use such, approaches helps diabetics to better control their blood glucose levels within normal range since they can now time their insulin injection based on when they eat a meal. GE time can also be used to titrate the dose and type of insulin or other glucose regulating agents. For example for slower times they may want to take a lower dose of insulin so that they do not become too hypoglycemic and vice versa (e.g., higher doses for faster GE-times so they do not become hyperglycemic). The recommended administration times can be incorporated into algorithms in software module of the receiving unit described herein. Other medications which can be so timed and adjusted include incretins such as various GLP-1 incretins including, for example Exenatide, available under the tradename BYETTA. Other factors which can be used in conjunction with GE times in adjusting or titrating the dose and timing of the glucose regulating compound can include the half-life of the particular glucose regulating agent. So, for example, such agents having shorter half-lives can be taken sooner after eating a meal than those with longer half-lives.

Additional GE Parameters and their Uses

In addition to measurement of Gastric Emptying time, embodiments of the invention also contemplate measure of a number of other Gastric Emptying and other GI tract related parameters. These parameters include one or more of the following: GE velocity, the speed at which food/stomach contents moves from the stomach to the small intestine; average GE velocity; peak GE velocity; number of peristaltic contractions occurring in the stomach and/or small intestine which are exerted on the capsule/food during gastric emptying; GET to peristaltic contraction ratio; which is the ratio of GE time per number of peristaltic contractions; average and peak peristaltic forces exerted by the stomach and/or small intestine on capsule/food during the transit of food from the stomach to the small intestine; and GET to average peristaltic force ratio, which is ratio of GET per average force of peristaltic contraction occurring prior to or during the transit of food from the stomach to the small intestine. The determination of theses parameters may be done by programming (e.g., software modules) or other logic resident in a controller on the capsule (e.g., controller 60) or the external receiving device (e.g., controller 35). Measurement of GE velocity may be facilitated by including one or more sensors 10S on or in capsule 10 for making various measurements as shown in FIGS. 1A, 1b and 2b. In various embodiments, sensor 10S may correspond to an accelerometer for providing velocity and acceleration data of the capsule in the GI tract; and a force sensor such as a strain gauge for providing data including the magnitude of peristaltic forces exerted on the capsule as well as the number of peristaltic contractions exerted on the capsule during gastric emptying or other period of time in the digestive period. The output of these sensors can be coupled to controller 60 and/or transmitter 80 which then generate a signal encoding measured data by the sensors (e.g. force, velocity, etc.) for transmission to receiver 33 on the receiver unit 30 or other external receiving device, e.g., device 40. These and other GE parameters can be used for one or more of the following clinical applications: i) diagnosis of gastroparesis or other like condition; ii) diagnosis of irritable bowel syndrome by an above average number of peristaltic contractions and/or increase in GE velocities; iii) providing information that the patient may use to titrate or adjust the timing and dose of the administration of medication before, during or after eating a meal; iv) providing information that the patient may use to titrate or adjust the timing and dose of insulin or other glucose regulating before, during or after eating a meal so that they may obtain improved control of their blood sugar levels and reducing the occurrence of hypoglycemia and hyperglycemia; and iv) providing information that the patient may use to titrate or adjust the timing and/or portion size of a meal particularly after a first or other prior meal or portion is eaten. Timing in this case being the time after a eating a prior meal or portion.

Conclusion

The foregoing description of various embodiments of the invention has been presented for purposes of illustration and description. It is not intended to limit the invention to the precise forms disclosed. Many modifications, variations and refinements will be apparent to practitioners skilled in the art. For example, the capsule can be sized and otherwise configured for various pediatric applications. Also, in some embodiments, the capsule coating can be configured to degrade in the large intestine so that transit times from the stomach to the large intestine can be measured. Further, in some embodiments, the capsule can include four electrodes with the third covered by a coating that degrades in the small intestine and a fourth which degrades in the large intestine so that transit times from the small to the large intestine can be measured. In use, such embodiments provide the clinician has a linear map of transit times between specific organs within the GI tract as well overall transit times. Additionally, various embodiments of the capsule can include two way telemetry for signaling to and from an external monitoring and/or control device, such as embodiments of the receiving device described herein. Also, in alternative embodiments, in place of electrodes, the capsule may includes a pH sensor for determining where the capsule is in the intestinal tract based on the pH in the respective location (e.g., the stomach or small intestine). So for example, a pH reading in the range of about 1.5 to 3.5 would indicate the capsule was in the stomach and a pH of above about 6 or 6.5 would indicate the capsule is in the small intestine.

Elements, characteristics, or acts from one embodiment can be readily recombined or substituted with one or more elements, characteristics or acts from other embodiments to form numerous additional embodiments within the scope of the invention. Moreover, elements that are shown or described as being combined with other elements, can, in various embodiments, exist as standalone elements. Further still, it should be appreciated that every recitation of an element, component, compound, value, characteristic or acts, also means that embodiments are contemplated which specifically excludes those elements, components, compounds, etc. Hence, the scope of the present invention is not limited to the specifics of the described embodiments, but is instead limited solely by the appended claims.

What is claimed is:

1. A swallowable capsule for measurement of a gastric emptying parameter, the capsule comprising:
    a capsule body sized to be swallowed and pass through the intestinal track of a patient, the capsule body having an outer surface and defining a capsule body interior;
    at least a first, second and third electrode disposed on the capsule body outer surface; an enteric coating disposed over a portion of the capsule body outer surface including the third electrode, the coating configured to electrically insulate the third electrode while in the stomach and degrade in response to a selected pH in the small intestine to expose the third electrode;
    a first circuit electrically coupled to the first and second electrodes, the first circuit configured to generate a first input signal based on a current between the first and second electrodes; a second circuit electrically coupled to the second and third electrodes, the second circuit configured to generate a second input signal based on a current between the second and third electrodes;
    a controller operatively coupled to the first and second circuits, the controller disposed within the capsule body interior and configured to generate a driver signal sent to the second electrode and receive the first and second input signals from the first and second circuits, to generate a first output signal in response to the first input signal and a second output signal in response to the second input signal, to determine a time of passage of the capsule between the stomach and the intestines based upon the first and second output signals, and to determine the gastric emptying parameter based on the time of passage;
    a power source coupled to at least one of the controller, the first circuit and second circuits; and wherein when the capsule reaches the stomach, the first and second electrodes electrically couple with stomach fluids to allow current flow between the first and second electrodes to generate the first input signal and when the capsule reaches the small intestine the enteric coating degrades allowing the second and third electrodes to couple with fluid in the small intestine to allow current flow between the second and third electrodes to generate the second input signal.

2. The capsule of claim 1, wherein the enteric coating comprises copolymers derived from esters of acrylic and methacrylic.

3. The capsule of claim 1, wherein the power source is a battery, a lithium battery, a lithium ion battery or an alkaline battery.

4. The capsule of claim 1, wherein the driver signal is an alternating current (AC) signal.

5. The capsule of claim 1, wherein the controller comprises a processor or microprocessor.

6. The capsule of claim 1, wherein the first and second input signals comprise a voltage.

7. The capsule of claim 1, wherein the first and second circuits include an operational amplifier (opamp).

8. The capsule of claim 7, wherein the opamp is coupled to the first or second electrode and the controller.

9. The capsule of claim 1, wherein the first and second circuits include a resistor.

10. The capsule of claim 9, wherein the resistor has a value greater than 1 mega ohm.

11. The capsule of claim 9, wherein the resistor includes a first and second resistor.

12. The capsule of claim 1, wherein the controller is configured to discontinue the first output signal after a selected period of time.

13. The capsule of claim 12 wherein the selected period of time is between 1 to 10 seconds.

14. The capsule of claim 1, wherein the controller is configured to discontinue the second output signal after a selected period of time.

15. The capsule of claim 14, wherein the selected period of time is between 1 to 10 seconds.

16. The capsule of claim 1, wherein an amplitude of the first output signal decreases after the controller starts generating the second output signal.

17. The capsule of claim 16, wherein the first output signal amplitude is a voltage amplitude.

18. The capsule of claim 17, wherein the voltage amplitude of the first output signal decreases by a factor of 2.

19. The capsule of claim 1, wherein the first output signal corresponds to a first chirp signal.

20. The capsule of claim 19, wherein the second output signal corresponds to a second chirp signal.

21. The capsule of claim 1, further comprising a transmitter coupled to the controller, the transmitter configured to transmit the first or second output signal.

22. The capsule of claim 21, wherein the transmitter is integral to the controller.

23. The capsule of claim 21, wherein the transmitter is a radiofrequency (RF) transmitter.

24. The capsule of claim 21, wherein the transmitter comprises a power amplifier.

25. The capsule of claim 1, wherein the controller includes logic to determine at least one of a start time of at least one of the first or second output signals or a gastric emptying parameter.

26. The capsule of claim 25, wherein the gastric emptying parameter is a gastric emptying time, an average gastric emptying time, a gastric emptying time with food, a gastric emptying time for a selected meal type, or a gastric emptying time for a selected meal portion.

27. The capsule of 25, where the gastric emptying time is determined based on the start time of the first and second output signals.

28. The capsule of claim 25, wherein the controller is configured to generate signals encoding information on the start time of the least one or second output signals or the gastric emptying time, the encoding signals being transmittable by the controller or a transmitter coupled to the controller.

29. The capsule of claim 1, wherein the selected pH is above 6.

30. The capsule of claim 29, wherein the selected pH is above 6.5.

31. The capsule of claim 1, wherein a density of the capsule is in a range from 0.5 to 1.5 gram/cc.

32. The capsule of claim 31, wherein a density of the capsule is in a range from 0.8 to 1.2 gram/cc.

33. The capsule of claim 32, wherein the density of the capsule is 1 gram/cc.

34. The capsule of claim 1, wherein a surface tension of the capsule body outer walls is in a range from 30 to 45 dynes/cm.

35. The capsule of claim 34, wherein a surface tension of the capsule body outer walls is in a range from 30 to 31 dynes/cm.

36. A swallowable capsule for measurement of gastric emptying time, the capsule comprising:
    a capsule body sized to be swallowed and pass through the intestinal track of a patient, the capsule body having an outer surface and defining a capsule body interior;
    at least a first, second and third electrodes disposed on a capsule body outer surface; and
    an enteric coating disposed over a portion of the capsule body outer surface including the third electrode, the coating configured to cover the third electrode while in the stomach and degrade in response to a selected pH in the small intestine to expose the third electrode;
    a first circuit electrically coupled to the first and second electrodes, the first circuit configured to generate a first input signal based on a current between the first and second electrodes; a second circuit electrically coupled to the second and third electrodes, the second circuit configured to generate a second input signal based on a current between the second and third electrodes; a controller coupled to the first and second circuits, the controller disposed within the capsule body interior and configured to generate a driver signal sent to the second electrode and receive the signals from the first and second circuits, to generate a first output signal in response to the first input signal and a second output signal in response to the second input signal to determine a time of passage of the capsule between the stomach and the intestines based upon the first and second output signals, and to determine the gastric emptying parameter based on the time of passage;
    a transmitter coupled to the controller for transmitting the first and second output signals;
    a power source coupled to at least one of the controller, the first circuit or second circuits or the transmitter; and
    wherein when the capsule reaches the stomach, the first and second electrodes electrically couple with stomach fluids to allow current flow between the first and second electrodes to generate the first input signal and when the capsule reaches the small intestine the enteric coating degrades allowing the second and third electrodes to couple with fluid in the small intestine to allow current flow between the second and third electrodes to generate the second input signal.

37. The capsule of claim 36, wherein the transmitter is an RF transmitter.

38. A system for measuring a gastric emptying parameter, the system comprising: the capsule of claim 36; and a receiver unit for receiving the transmitted first and second output signals.

39. The system of claim 38, wherein the receiver unit is configured to be worn by the patient.

40. The system of claim 39, further comprising a patch configured to be worn on the patient's abdomen, the receiver unit positioned on the patch.

41. The system of claim 40, wherein the patch is configured to adhere to the patient's skin.

42. The system of claim 41, wherein the patch is sufficiently flexible to bend and flex with movement of the patients abdomen and stay adhered to the skin with the receiver unit attached.

43. The system of claim 38, further comprising a controller operatively coupled to the receiver unit, the controller configured to determine the gastric emptying parameter utilizing the first and second output signals.

44. The system of claim 38, wherein the first and second output signals provide information on a location of the capsule in a GI tract at a moment in time.

45. The system of claim 38, wherein determined gastric parameter is a gastric emptying time.

* * * * *

UNITED STATES PATENT AND TRADEMARK OFFICE
CERTIFICATE OF CORRECTION

| | | |
|---|---|---|
| PATENT NO. | : 11,103,187 B2 | |
| APPLICATION NO. | : 16/006093 | |
| DATED | : August 31, 2021 | |
| INVENTOR(S) | : Mir A. Imran | |

It is certified that error appears in the above-identified patent and that said Letters Patent is hereby corrected as shown below:

In the Claims

Claim 1, at Column 23, Line 40, please delete "track" and insert --tract--.
Claim 1, at Column 23, Line 42, please delete "second, and third" and insert --a second, and a third--.
Claim 1, at Column 24, Line 2, please delete "circuit and second circuits" and insert --circuit, and the second circuit--.
Claim 27, at Column 25, Line 6, please delete "of 25, where the" and insert --of claim 25, where a--.
Claim 28, at Column 25, Line 11, please delete "or the" and insert --or a--.
Claim 28, at Column 25, Lines 12-13, please delete "transmittable" and insert --transmitted--.
Claim 31, at Column 25, Line 20, please delete "gram/cc" and insert --gram/cm$^3$--.
Claim 32, at Column 25, Line 22, please delete "gram/cc" and insert --gram/cm$^3$--.
Claim 33, at Column 25, Line 24, please delete "gram/cc" and insert --gram/cm$^3$--.
Claim 36, at Column 25, Line 34, please delete "track" and insert --tract--.
Claim 36, at Column 25, Line 36, please delete "second and third electrodes" and insert --a second, and a third electrode--.
Claim 36, at Column 25, Lines 36-37, please delete "a capsule body" and insert --the--.
Claim 36, at Column 25, Line 38, please delete "capsule body".
Claim 36, at Column 26, Line 14, please delete "circuit or second circuits" and insert --circuit, the second circuit,--.
Claim 45, at Column 26, Line 48, please delete "wherein determined" and insert --wherein the determined--.

Signed and Sealed this
Twenty-third Day of August, 2022

Katherine Kelly Vidal
*Director of the United States Patent and Trademark Office*